US009555171B2

(12) United States Patent
Sengun et al.

(10) Patent No.: US 9,555,171 B2
(45) Date of Patent: Jan. 31, 2017

(54) METHODS AND DEVICES FOR COLLECTING SEPARATE COMPONENTS OF WHOLE BLOOD

(75) Inventors: Mehmet Ziya Sengun, Raynham, MA (US); William Parrish, Raynham, MA (US); Brooks J. Story, Raynham, MA (US); Kristian DiMatteo, Raynham, MA (US); Gregory R. Whittaker, Raynham, MA (US); Douglas Allen Fifolt, Raynham, MA (US)

(73) Assignee: DEPUY MITEK, LLC, Raynham, MA (US)

( * ) Notice: Subject to any disclaimer, the term of this patent is extended or adjusted under 35 U.S.C. 154(b) by 1375 days.

(21) Appl. No.: 12/894,271

(22) Filed: Sep. 30, 2010

(65) Prior Publication Data
US 2012/0082652 A1    Apr. 5, 2012

(51) Int. Cl.
| A01N 1/02 | (2006.01) |
| B01D 21/26 | (2006.01) |
| B01D 21/00 | (2006.01) |
| A61M 1/02 | (2006.01) |
| A61M 1/36 | (2006.01) |
| B01L 3/00 | (2006.01) |

(52) U.S. Cl.
CPC .......... *A61M 1/029* (2013.01); *A61M 1/3693* (2013.01); *B01L 3/5021* (2013.01); *A61M 2202/0427* (2013.01); *B01D 21/262* (2013.01); *B01D 2221/10* (2013.01); *B01L 2300/028* (2013.01); *B01L 2400/0409* (2013.01); *B01L 2400/0478* (2013.01); *B01L 2400/0622* (2013.01)

(58) Field of Classification Search
CPC ................ A61M 1/029; A61M 1/3693; A61M 2202/0427; B01D 21/262; A01N 1/02
USPC .................. 435/2; 494/37; 422/527
See application file for complete search history.

(56) References Cited

U.S. PATENT DOCUMENTS

| 4,185,629 A | 1/1980 | Cullis |
| 4,187,979 A | 2/1980 | Cullis |
| 4,268,393 A | 5/1981 | Persidsky |
| 4,269,718 A | 5/1981 | Persidsky |
| 4,322,298 A | 3/1982 | Persidsky |
| 4,421,503 A | 12/1983 | Latham, Jr. |
| 4,424,132 A | 1/1984 | Iriguchi |
| 4,427,651 A | 1/1984 | Stroetmann |
| 4,529,706 A | 7/1985 | Horres, Jr. |
| 4,530,691 A | 7/1985 | Brown |
| 4,608,178 A | 8/1986 | Johansson |
| 4,663,032 A | 5/1987 | Loos |
| 4,680,025 A | 7/1987 | Kruger |
| 4,713,060 A * | 12/1987 | Riuli ............................. 604/199 |
| 4,720,284 A * | 1/1988 | McCarty ........................ 494/37 |
| 4,828,716 A | 5/1989 | McEwen |
| 4,871,462 A | 10/1989 | Fischel |
| 4,874,385 A * | 10/1989 | Moran et al. ................. 604/208 |
| 4,904,396 A | 2/1990 | Benet |
| 4,927,545 A | 5/1990 | Roginski |
| 4,944,883 A | 7/1990 | Schoendorfer |
| 5,073,378 A | 12/1991 | Shoshan |
| 5,102,407 A | 4/1992 | Carmen |
| 5,154,716 A | 10/1992 | Bauman |
| 5,234,608 A | 8/1993 | Duff |
| 5,258,126 A | 11/1993 | Pall |
| 5,318,782 A | 6/1994 | Weis Fogh |
| 5,370,802 A | 12/1994 | Brown |
| 5,456,824 A | 10/1995 | Misumi |
| 5,510,102 A | 4/1996 | Cochrum |
| 5,527,472 A | 6/1996 | Bellotti |
| 5,550,060 A | 8/1996 | Saunders |
| 5,580,465 A | 12/1996 | Pall |
| 5,585,007 A | 12/1996 | Antanavich |
| 5,589,462 A | 12/1996 | Patat |
| 5,601,727 A | 2/1997 | Bormann |
| 5,607,694 A | 3/1997 | Marx |
| 5,614,106 A | 3/1997 | Payrat |
| 5,631,019 A | 5/1997 | Marx |
| 5,651,982 A | 7/1997 | Marx |
| 5,733,545 A | 3/1998 | Hood, III |
| 5,824,228 A | 10/1998 | Bolomier |
| 5,858,253 A | 1/1999 | Holm |
| 5,899,874 A | 5/1999 | Jonsson |
| 5,993,657 A | 11/1999 | Williams |
| 6,010,627 A | 1/2000 | Hood, III |
| 6,022,306 A | 2/2000 | Dumont |
| 6,153,148 A | 11/2000 | Thomas |
| 6,214,338 B1 | 4/2001 | Antanavich |
| 6,277,556 B1 | 8/2001 | Grode |
| 6,284,285 B1 | 9/2001 | Weis-Fogh |
| 6,296,602 B1 | 10/2001 | Headley |
| 6,303,112 B1 | 10/2001 | Worden |
| 6,322,785 B1 | 11/2001 | Landesberg |

(Continued)

FOREIGN PATENT DOCUMENTS

| WO | WO 2008016574 | 2/2008 |
| WO | WO 2009002849 | 12/2008 |

OTHER PUBLICATIONS

Kajikawa et al. Platelet-Rich Plasma Enhances the Initial Mobilization of Circulation-Derived Cells for Tendon Healing; Journal of Cellular Physiology, vol. 215 (2008) pp. 837-845.*

*Primary Examiner* — Scott Long
*Assistant Examiner* — Paul Martin

(57) ABSTRACT

A method provides for procuring platelet rich plasma (PRP) from a sample of whole blood in a vial. The method includes the steps of: separating the whole blood into layers through centrifugation with an upper layer containing platelet poor plasma (PPP) and a PRP layer below the upper layer containing PRP; adjusting an end point of a first range of motion of an extractor relative to a position of the PRP layer; moving the extractor through the first range of motion through the vial, PPP passing out from the upper layer through the extractor; and after the extractor reaches the end point of the first range of motion, extracting the PRP through the extractor and collecting the PRP.

10 Claims, 23 Drawing Sheets

(56) References Cited

U.S. PATENT DOCUMENTS

| | | |
|---|---|---|
| 6,325,750 B1 | 12/2001 | Jorgensen |
| 6,342,157 B1 | 1/2002 | Hood, III |
| 6,398,972 B1 | 6/2002 | Blasetti |
| 6,413,200 B1 | 7/2002 | Jorgensen |
| 6,432,119 B1 | 8/2002 | Saadat |
| 6,444,228 B1 | 9/2002 | Baugh |
| 6,475,175 B1 | 11/2002 | Rivera |
| 6,497,823 B1 | 12/2002 | Rothman |
| 6,524,568 B2 | 2/2003 | Worden |
| 6,579,219 B2 | 6/2003 | Dolecek |
| 6,582,349 B1 | 6/2003 | Cantu |
| 6,582,350 B2 | 6/2003 | Dolecek |
| 6,592,507 B2 | 7/2003 | Jorgensen |
| 6,596,180 B2 | 7/2003 | Baugh |
| 6,596,181 B2 | 7/2003 | Dolecek |
| 6,605,028 B2 | 8/2003 | Dolecek |
| 6,605,223 B2 | 8/2003 | Jorgensen |
| 6,610,002 B2 | 8/2003 | Dolecek |
| 6,613,566 B2 | 9/2003 | Kandler |
| 6,649,072 B2 | 11/2003 | Brandt |
| 6,719,901 B2 | 4/2004 | Dolecek |
| 6,752,777 B1 | 6/2004 | Takagi |
| 6,773,923 B2 | 8/2004 | Patzke |
| 6,780,333 B1 | 8/2004 | Brown |
| 6,790,371 B2 | 9/2004 | Dolecek |
| 6,793,828 B2 | 9/2004 | Dolecek |
| 6,811,777 B2 | 11/2004 | Mishra |
| 6,827,863 B2 | 12/2004 | Dolecek |
| 6,830,762 B2 | 12/2004 | Baugh |
| 6,835,316 B2 | 12/2004 | Dolecek |
| 6,835,353 B2 | 12/2004 | Smith |
| 6,841,170 B2 | 1/2005 | Sacchi |
| 6,852,330 B2 | 2/2005 | Bowman |
| 6,855,119 B2 | 2/2005 | Rivera |
| RE38,730 E | 4/2005 | Gann |
| 6,884,428 B2 | 4/2005 | Binette |
| 6,890,728 B2 | 5/2005 | Dolecek |
| 6,893,412 B2 | 5/2005 | Saito |
| 6,899,666 B2 | 5/2005 | Brown |
| 6,899,813 B2 | 5/2005 | Dolecek |
| RE38,757 E | 7/2005 | Gann |
| 6,939,329 B1 | 9/2005 | Verkaart |
| 6,942,639 B2 | 9/2005 | Baugh |
| 6,942,880 B1 | 9/2005 | Dolecek |
| 6,945,411 B1 | 9/2005 | Bormann |
| 6,951,612 B2 | 10/2005 | Dolecek |
| 6,964,685 B2 | 11/2005 | Murray |
| 6,979,307 B2 | 12/2005 | Beretta |
| 6,981,991 B2 | 1/2006 | Ferree |
| 6,982,038 B2 | 1/2006 | Dolecek |
| 7,005,136 B2 | 2/2006 | Nathan |
| 7,011,852 B2 | 3/2006 | Sukavaneshvar |
| 7,026,374 B2 | 4/2006 | Nathan |
| 7,060,018 B2 | 6/2006 | Skinkle |
| 7,077,273 B2 | 7/2006 | Ellsworth |
| 7,112,342 B2 | 9/2006 | Worden |
| 7,137,996 B2 | 11/2006 | Steiner |
| 7,141,066 B2 | 11/2006 | Steiner |
| 7,156,803 B2 | 1/2007 | Voellmicke |
| 7,179,391 B2 | 2/2007 | Leach |
| 7,189,410 B1 | 3/2007 | Drohan |
| 7,192,604 B2 | 3/2007 | Brown |
| 7,196,054 B1 | 3/2007 | Drohan |
| 7,223,346 B2 | 5/2007 | Dorian |
| 7,252,758 B2 | 8/2007 | Dolecek |
| 7,285,266 B2 | 10/2007 | Vournakis |
| 7,291,450 B2 | 11/2007 | Sowemimo-Coker |
| 7,300,439 B2 | 11/2007 | May |
| 7,306,555 B2 | 12/2007 | Dolecek |
| 7,306,741 B2 | 12/2007 | Dolecek |
| 7,309,356 B2 | 12/2007 | Steiner |
| 7,316,822 B2 | 1/2008 | Binette |
| 7,347,948 B2 | 3/2008 | Dolecek |
| 7,354,415 B2 | 4/2008 | Bainbridge |
| 7,361,277 B2 | 4/2008 | Bormann |
| 7,374,678 B2 | 5/2008 | Leach |
| 7,396,451 B2 | 7/2008 | Holmes |
| 7,413,652 B2 | 8/2008 | Dolecek |
| 7,413,665 B2 | 8/2008 | Holmes |
| 7,442,178 B2 | 10/2008 | Chammas |
| 7,450,224 B2 | 11/2008 | Maroney |
| 7,452,344 B2 | 11/2008 | Jorgensen |
| 7,465,285 B2 | 12/2008 | Hutchinson |
| 7,470,371 B2 | 12/2008 | Dorian |
| 7,497,944 B2 | 3/2009 | Högberg |
| 7,503,889 B2 | 3/2009 | Briggs |
| 7,740,760 B2 | 6/2010 | Coull |
| 2003/0007957 A1* | 1/2003 | Britton et al. ............ 424/93.72 |
| 2003/0205538 A1 | 11/2003 | Dorian |
| 2004/0065324 A1 | 4/2004 | Woo |
| 2006/0074394 A1 | 4/2006 | Beretta |
| 2006/0175244 A1 | 8/2006 | Dorian |
| 2007/0131612 A1 | 6/2007 | Duffy |
| 2008/0199513 A1 | 8/2008 | Beretta |
| 2008/0199900 A1 | 8/2008 | Signore |
| 2008/0217264 A1 | 9/2008 | Leach |
| 2008/0217265 A1 | 9/2008 | Leach |
| 2008/0283474 A1 | 11/2008 | Leach |
| 2009/0014391 A1 | 1/2009 | Leach |
| 2009/0100942 A1 | 4/2009 | Maeda |
| 2009/0101599 A1 | 4/2009 | Dorian |
| 2009/0250413 A1 | 10/2009 | Hoeppner |
| 2010/0012592 A1 | 1/2010 | Carter |
| 2010/0140182 A1 | 6/2010 | Chapman |

* cited by examiner

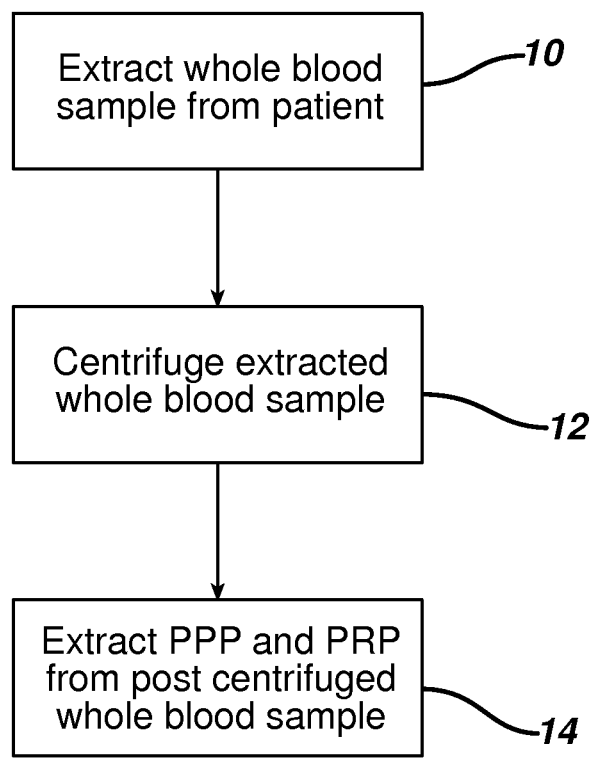

METHODS AND DEVICES FOR COLLECTING SEPARATE COMPONENTS OF WHOLE BLOOD

BACKGROUND OF THE INVENTION

The present invention relates to methods and devices for collecting separate components of whole blood.

Platelets have been known to play critical roles in hemostasis and wound healing through a multitude of complex biological functions and interactions. In clinical applications, platelets are used in elevated concentrations known as platelet rich plasma (PRP).

SUMMARY

A method according to the present invention provides for procuring platelet rich plasma (PRP) from a sample of whole blood in a vial. The method comprises the steps of: separating the whole blood into layers through centrifugation with an upper layer containing platelet poor plasma (PPP) and a PRP layer below the upper layer containing PRP; adjusting an end point of a first range of motion of an extractor relative to a position of the PRP layer; moving the extractor through the first range of motion through the vial, PPP passing out from the upper layer through the extractor; and after the extractor reaches the end point of the first range of motion, extracting the PRP through the extractor and collecting the PRP.

Preferably, the step of adjusting the end point of the first range of motion comprises setting the position of a stop against which an abutment associated with the extractor engages at the end point.

Preferably, the extractor comprises a piston sized to tightly fit through the vial and wherein the PPP passes out of the upper layer through an orifice in the piston. In one aspect of the invention the step of extracting the PRP comprises moving the piston beyond the end point of the first range of motion through a second range of motion and passing the PRP through the orifice while moving the extractor through the second range of motion. Preferably, the PPP is passed through a first flow path as the extractor moves through the first range of motion and a diverter is engaged as the extractor reaches the end point, the diverter sending the PRP through a separate second flow path. For instance, an abutment associated with the extractor can engage a lever on the diverter as the extractor reaches the end point to send flow from the extractor through the second flow path. Preferably, the diverter comprises a three-way valve.

In one aspect of the invention, the orifice is disposed at a distal tip of a needle in the extractor.

In one aspect of the invention a handle is associated with the extractor and a user in one continuous motion, by pressing on the handle, moves the extractor through the first range of motion and the second range of motion.

In one aspect of the invention, the step of extracting the PRP comprises passing a tip of a needle through the orifice to the PRP layer and extracting the PRP through the needle.

Preferably, the sample of whole blood is collected from a patient and further comprising the step of applying the PRP to a site on the patient's body to promote healing.

A device according to the present invention provides for collecting platelet rich plasma (PRP) from a sample in a vial of centrifugally fractionated whole blood having an upper layer comprising platelet poor plasma and a PRP layer containing the PRP. The device comprises an extractor movable through the vial in a first adjustable range of motion, the first range of motion having an end point associated with a position of the PRP. An adjustment between the extractor and the vial adjusts the end point of the range of motion to correspond to the position of the PRP. A first extraction flow path through the extractor is associated with the first range of motion, the extractor being adapted to flow the PPP through the first extraction flow path as the extractor moves through the first range of motion and a second extraction flow path is associated with the first range of motion end point, the second extraction flow path leading to a PRP collection receptacle.

Preferably, the device further comprises a stop associated with the vial and an abutment associated with the extractor, the abutment engaging the stop at the end point.

Preferably, the extractor comprises a piston sized to tightly fit through the vial wherein the PPP passes out of the upper layer through an orifice in the piston.

In one aspect of the invention the extractor further comprises a second range of motion beyond the end point of the first range of motion, the second extraction flow path being associated with the second range of motion. Preferably, a diverter is disposed between the extractor and the first extraction flow path and between the extractor and the second extraction flow path, the diverter being operable between a first diverter position in which to divert flow from the extractor through first extraction flow path while the extractor moves through the first range of motion and a second diverter position in which to divert flow through the second extraction flow path after the extractor reaches the end point of the first range of motion. For instance an abutment associated with the extractor can be provided and which is engageable with a lever on the diverter as the extractor reaches the end point of the first range of motion, the lever having a lever first position prior to engagement by the abutment wherein the diverter is in the diverter first position and a lever second position after engagement by the abutment wherein the diverter is in the diverter second position. Preferably, the diverter comprises a three-way valve.

In one aspect of the invention, the orifice is disposed at a distal tip of a needle in the extractor.

In one aspect of the invention, a handle is associated with the extractor, the handle being oriented to allow a user in one continuous motion, by pressing on the handle, to move the extractor through the first range of motion and the second range of motion.

In one aspect of the invention, an extraction needle extends through the orifice and the second extraction flow path extends through the extraction needle.

In one aspect of the invention, the device further comprises a housing having a holder for holding the vial and the extractor is connected to the housing. The adjustment can be adapted to move the holder relative to the housing.

BRIEF DESCRIPTION OF THE DRAWINGS

FIG. 1 is a flow chart illustrating the process of extracting PPP and PRP;

DETAILED DESCRIPTION OF THE PREFERRED EMBODIMENTS

FIG. 1 shows a process of separating whole blood into different components according to the present invention. At step 10, a whole blood sample is first extracted from a patient to a blood container. As the whole blood sample is extracted, it is mixed together with anticoagulant (typically 10-15% by volume) in the blood container. At step 12, the blood container is put into a centrifuge to undergo centrifugation, preferably at 3000 g level for 15 minutes. Any bench top centrifuge capable of handling 15 cc tubes can be used. After centrifugation, the whole blood sample will have three layers, a red blood cells layer at the bottom of the blood container; a buffy coat layer containing most of the platelets, resting on top of the red blood cells layer; a top layer with mostly plasma, resting on top of the buffy coat layer. The top layer is commonly referred to as platelet poor plasma (PPP) as the amount of platelets in it is almost non-existent. For purpose of the present invention, platelet rich plasma (PRP) is a mixture of some PPP, some red blood cells, and the entire amount of the buffy coat layer, as it is difficult to extract just the concentrated platelets in the buffy coat layer without also extracting any PPP or red blood cells. The PRP has a platelet concentration much higher than a base whole blood sample of the same volume (typically 4-5 folds over base blood). At step 14, the post centrifugation whole blood sample is directly placed into an extraction device and is separated into different components, specifically platelet poor plasma and platelet rich plasma.

Figure 2A:
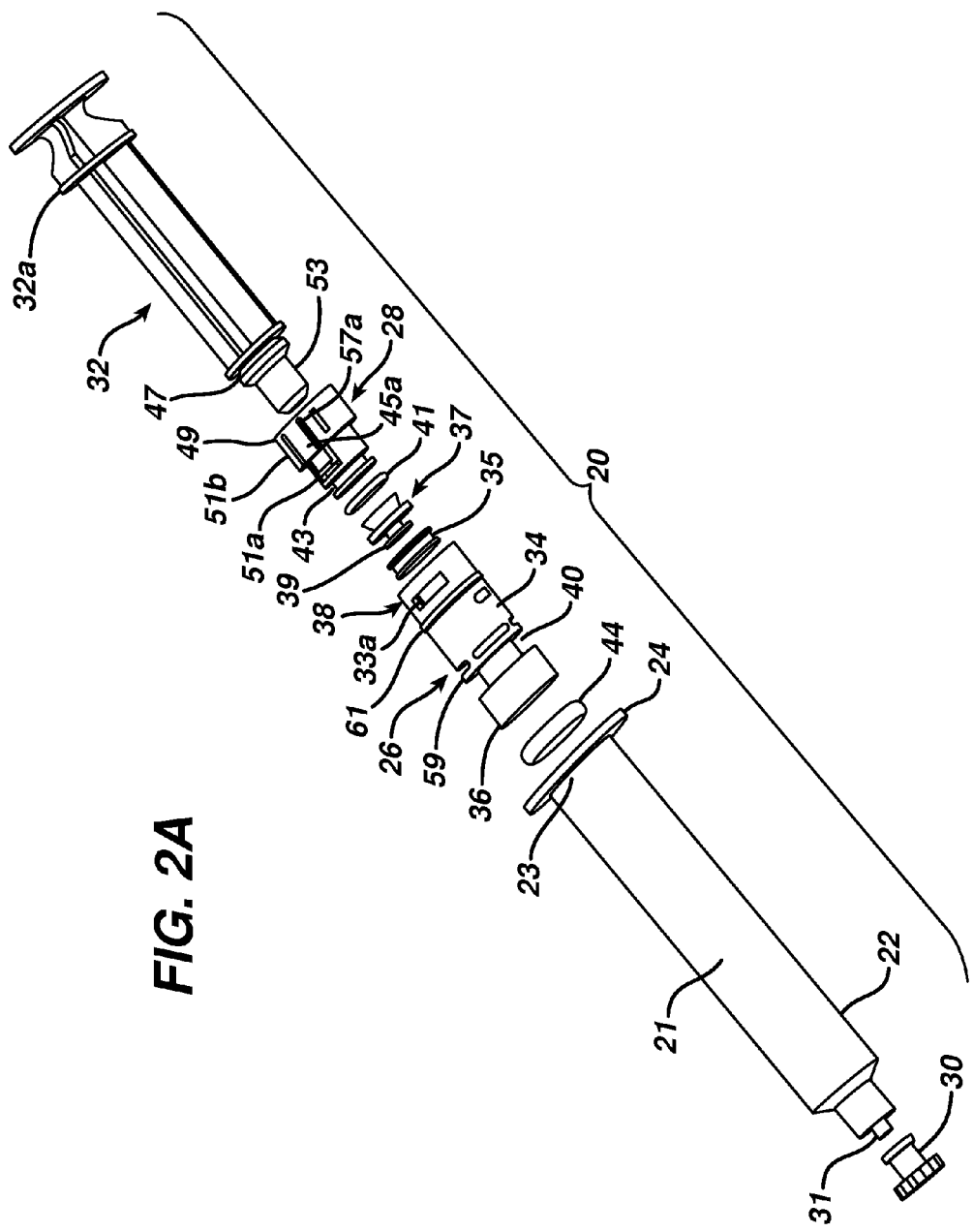
FIG. 2A is an exploded view of a blood container used in the extraction process in FIG. 1.
Figure 2B:
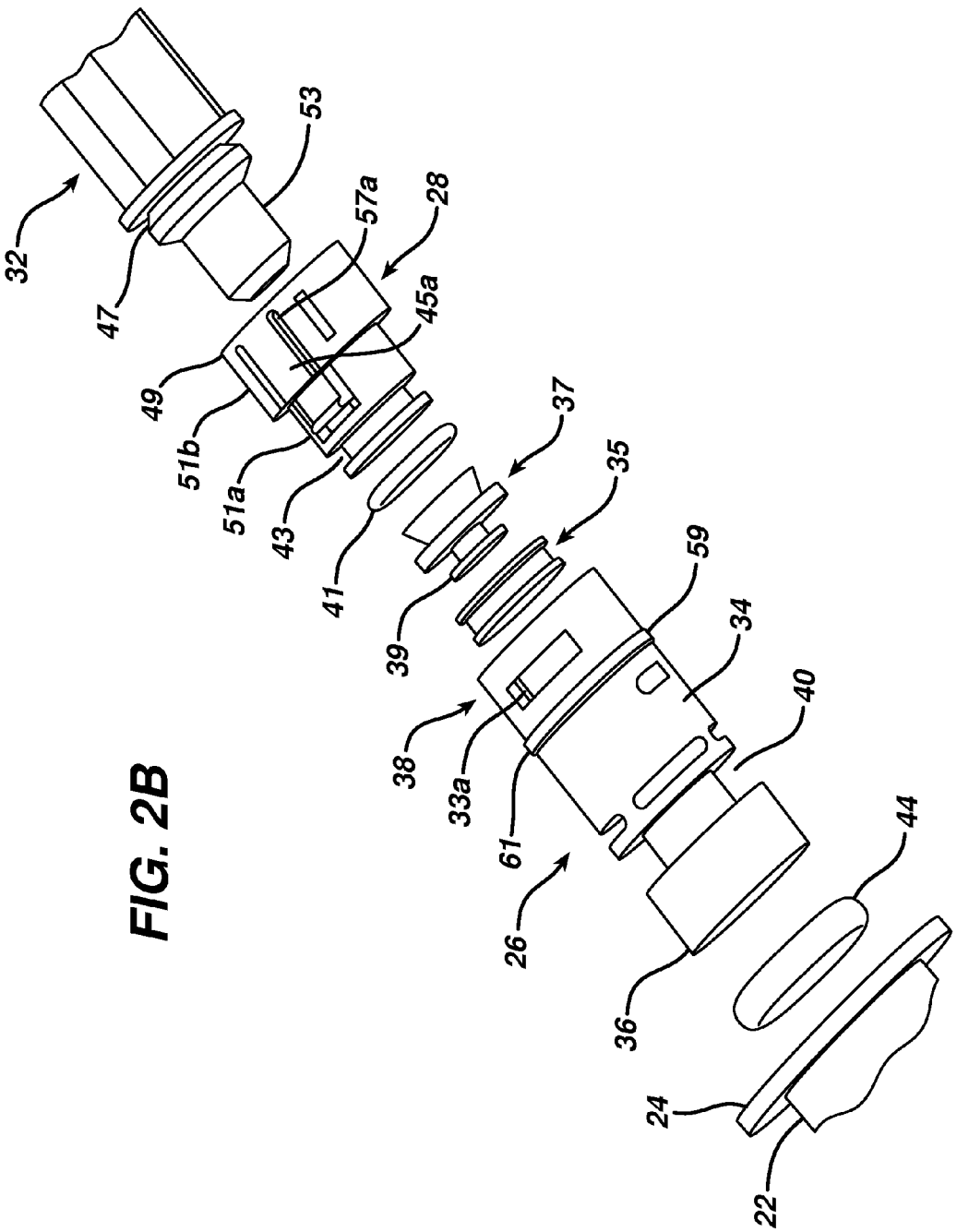
FIG. 2B is an enlarged view of the blood container in FIG. 2A.
Figure 2C:
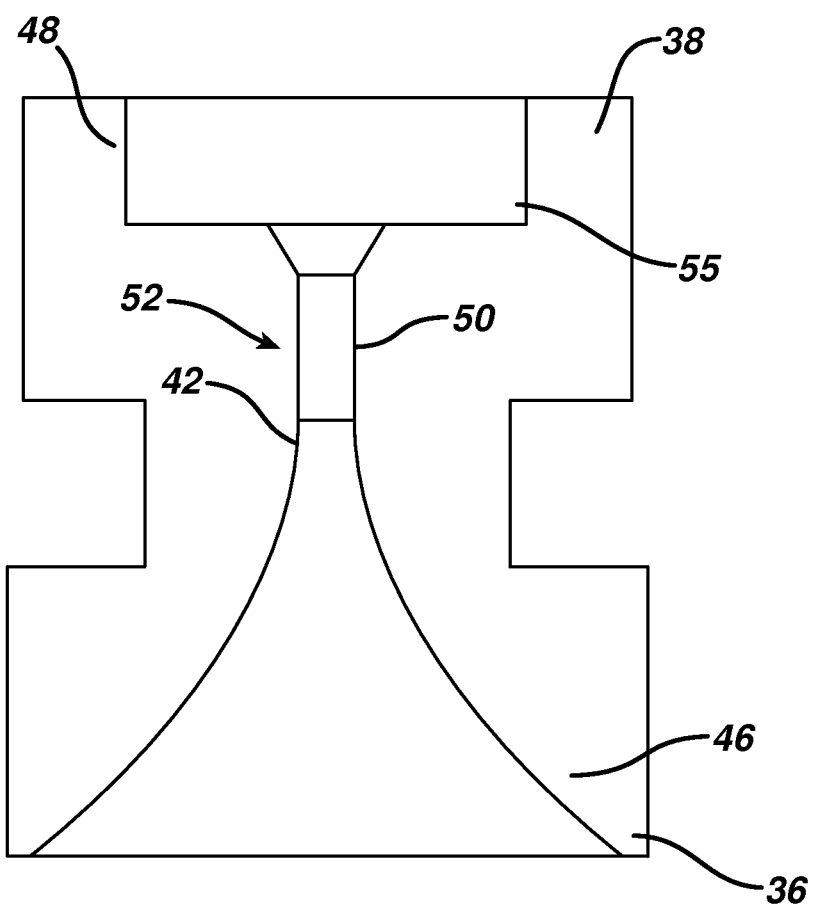
FIG. 2C is an enlarged view of the internal channel of the piston assembly in FIG. 2A.

FIGS. 2A-C depicts a blood container 20 used in steps 10-14 in FIG. 1 according to the present invention. In FIG. 2A, the blood container 20 has a syringe cap 30, a syringe barrel 22 with flange 24, a first seal 44, a piston assembly 26, a second seal 35, a needle guide 37, a third seal 41, a piston cap 28, and a removable plunger 32 that threads into the piston cap 28 fitted within. The syringe cap 30 is fitted over a distal tip 31 of the syringe barrel once the whole blood sample has been extracted from the patient and mixed with the anticoagulant and serves to prevent whole blood sample from leaking out of the blood container. In one embodiment a Becton, Dickinson and Company (BD) 10 cc syringe is used as the blood container 20 and other suitable syringes can be used without limitation. The syringe barrel 22 has a circular hollow chamber 21 with a raised rim 23 therewithin.

The piston assembly 26 is slidably fitted into the chamber 21 of the syringe barrel 22. The piston assembly has a main body 34 with a distal end 36 and a proximal end 38. The main body 34 has an outer slot 40 near the distal end, aperture 33a and 33b (not shown) located on opposite side of the main body near respectively near the proximal end, and an inner channel 42 (as seen in FIG. 2B). The first seal 44 is fitted onto the outer slot to keep the whole blood sample from spilling out of the syringe barrel. The inner channel 42 of the main body 34 has also a distal end 48 and a proximal end 46. The inner channel 42 has a generally an hour-glass shape with a seal 50 located at a neck portion 52 of the inner channel 42. The structure of the inner channel is discussed in more details in FIG. 2C.

The proximal end 38 of the main body 34 has an inner hollow area 55 (shown in FIG. 2C) that has the same diameter as the needle guide 37 and a lower portion 51 of the piston cap 28. The second seal 35 has an inner area (not shown) that is shaped to allow mounting onto a lower portion 39 of the needle guide 37, thus attaching the second seal onto the needle guide. The second seal serves to prevent the whole blood sample from spilling out of the syringe barrel. The needle guide 37 along with the second seal 35 are slidably received in the hollow area 55. The needle guide 37 has a central hollow channel (not shown) that is aligned with the inner channel 42 to allow an extraction needle to go through the needle guide and the piston assembly during the PPP and PRP extraction process discussed in more details below.

The piston cap 28 has a lower portion 51a, an upper portion 51b, and a pair of tabs 45a and 45b (not shown). Tab 45a and 45b are integrally formed with the piston cap 28 and are each defined by substantially u-shaped channels 57a and 57b (not shown) respectively. Tabs 45a and 45b are located on opposite sides of the piston cap.

The lower portion 51a has a slot 43. The third seal 41 mounts onto the slot 43 to prevent the whole blood sample from spilling out of the syringe barrel. The lower portion 51a along with the third seal 41 are slidably received in the hollow area 55 and attaches to the main body 34 by locking tabs 45a and 45b (now shown) into the apertures 33a and 33b (not shown) respectively. The plunger 32 attaches to the upper portion 51b of the piston cap 28. The upper portion 51b has a hollow inner area that is shaped to receive a lower portion 53 of the removable plunger 32. A lip portion 49 of the upper portion 51b clips onto a spherical portion 47 of the lower portion 53 to secure the removable plunger 32 to the piston cap 28. The syringe cap 30, the piston assembly 26, and the piston cap 28 together will help keep the whole blood sample sterile. The BD 10 cc syringe is available from Becton, Dickinson and Company of Franklin Lakes, N.J.

In one embodiment, before extracting the whole blood sample from the patient, a desired amount of anticoagulant is first extracted into the chamber 21 by conventional means. In order to prevent accidentally injection of the anticoagulant into the patient when extracting the whole blood sample, a skirt 32a located on the removable plunger 32 is used to limit the travel of the removable plunger 32 towards the distal end 31. The skirt 32a has a bigger diameter than the diameter of the chamber 22 such that when the removable plunger 32 is pushed towards the distal end 31, the removable plunger can only travel so far in the chamber 22 until the skirt 32a comes in contact with the flange 24. The location of the skirt 32a on the removable plunger 32 is chosen so that there will be enough room in the chamber 22 for the desire amount of anticoagulant when the skirt 32a comes in contact with the flange 24.

When extracting the whole blood sample from the patient, the removable plunger 32 is pulled away from the distal end 31, along with the piston assembly 26, and the piston cap 28 since they are all connected together. The dimensions of the piston assembly 26, the piston cap 28, and the removable plunger 32 are chosen so that when a skirt 61 on the main body 34 of the piston assembly 26 comes in contact with the raised rim 23, a predetermined volume of the whole blood sample has been extracted into the chamber 21. The blood container 20 will be disconnected from the patient and the syringe cap 30 is fitted over the distal tip 31 to prevent leakage of the whole blood sample.

When the skirt 61 comes in contact with the raised rim 23, the removable plunger 32 is stopped and the upper portion 51b of the piston cap 28 is exposed outside of the chamber 21 due to the dimensions of the piston assembly 26, the piston cap 28, and the removable plunger 32. This signals to a user who is extracting the whole blood sample that a predetermined volume has been extracted. Then the user can remove the removable plunger 32 from the blood container 20 by pulling the plunger away from the distal end 31. When the removable plunger 32 is pulled away from the distal end 31, the spherical portion 47 causes the upper portion 51b to expand outward, allowing the plunger to be separated from the piston cap. However, during the whole blood sample extraction, the upper portion is prevented from expanding outward by the chamber 21. Thus, removal of the removable plunger 32 is only possible after the upper portion 51 is outside of the chamber 21.

After removing the removable plunger 32, the blood container 20 containing the whole blood sample is centrifuged as in step 12 of FIG. 1. The piston cap 28 stays connected with the piston assembly 26 during centrifugation process to prevent contamination of the whole blood sample. After centrifugation, the piston cap 28 is removed from the piston assembly 26 by first pressing down on the tabs 45a and 45b inward towards each other to release the tabs from apertures 33a and 33b, then pulling the piston cap 28 away from the piston assembly 26. Then the blood container 20 can be placed into an extraction device to extract the PPP and PRP in accordance with the present invention.

FIG. 2C shows the structure of the inner channel of the piston assembly main body in FIG. 2A. The proximate end 48 and an enlarged distal end 46 of the inner channel 42 are enlarged, with the narrower neck portion 52 in between. The diameter of the distal end 46 gradually narrows up to the diameter of the neck portion 52. The gradual reduction in the diameter helps to guide the needle to pierce the seal 50. It also conforms to the way fluid flows during extraction, thus minimizing potential fluid entrapment in the inner channel.

Figure 3:
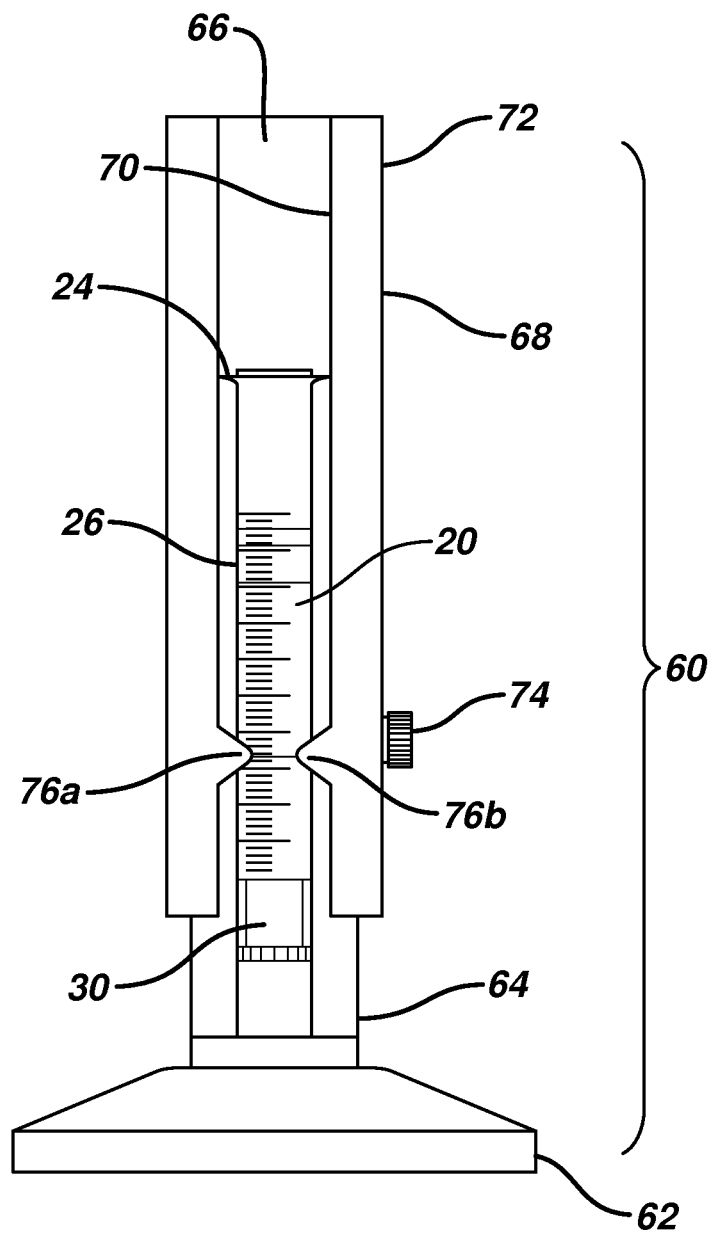
FIG. 3 is a front perspective view of an embodiment an extraction device according to the present invention.

FIG. 3 depicts an embodiment of an extraction device 60 used to extract the PPP and the PRP according to the present invention. The extraction device 60 has a base 62 supporting a main body 64. The base 62 and the main body 64 can be molded as one piece or separate pieces. The main body 64 has an inner channel 66. The inner channel 66 preferably has a width suitable to contain the blood container 20, but less than the flange 24 of the blood container so that when the blood container is inserted into the inner channel 66, the inner channel 66 will hold the blood container 20 above the base 62. A sleeve 68 has an inner portion 70 and an outer portion 72. The inner portion 70 slides onto the main body 64 and receives the flange 29. The sleeve 68 has a locking mechanism 74 that fixes the position of the sleeve relative to the main body 64. The locking mechanism 74 can be a turning knob that threads into both the sleeve and the main body 64, so that as the knob is turned towards the main body, the knob compresses on the sleeve 68 and the compression holds the sleeve 68 in a fixed position. Any other suitable locking mechanism can be used. A pair of pointers 76a, 76b are formed integrally with the sleeve 64 at a location on the sleeve 64 that is predetermined based on the amount of PRP to be extracted.

Figure 4A:
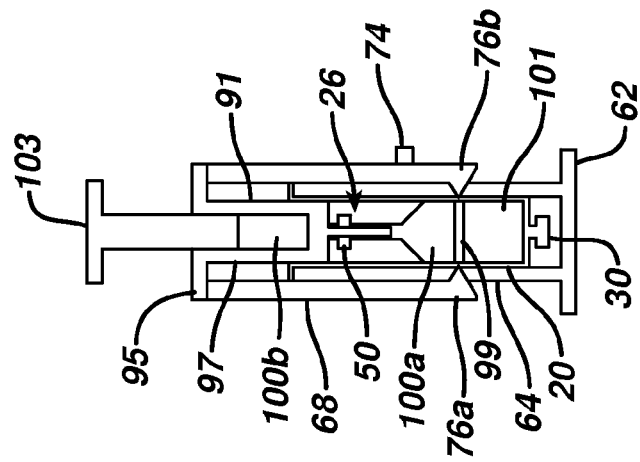
FIG. 4A is a plan view of aligning the buffy coat layer to the pointers in the extraction device.

FIGS. 4A-F depict an embodiment of the method of extracting PPP and PRP according to the present invention. In FIG. 4A, the blood container 20 containing the post centrifuged whole blood sample 98 having a red blood cells layer 101, a buffy coat layer 99, and a PPP layer 100, and the piston assembly 26 is first placed into the inner channel 66 of the main body 64 of the extraction device 60. The position of the sleeve 68 relative to the main body 64 is adjusted by aligning the point teeth 76a, 76b to the position of the buffy coat layer 99 in the blood container 20. The alignment of the buffy coat layer to the pointers 76a, 76b eliminates the variations in hematocrit between patients and ensures a predetermined amount of PRP will be extracted, because the distance between the top of the sleeve 68 and the location of the pointers 76a, 76b, the length of the needle 93, and the length of the needle 111, the length of the syringe barrel 105, the length of the syringe barrel 97 are chosen based on the predetermined PRP extraction volume. The locking mechanism 74 is then engaged to lock the sleeve 68 in place.

Figure 4B:
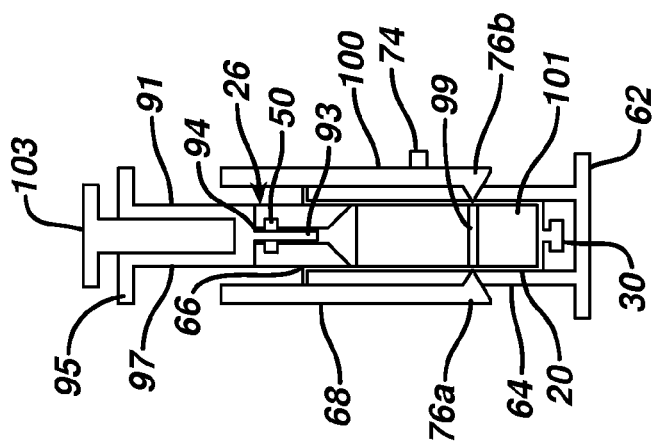
FIG. 4B is a plan view of inserting the PPP syringe into the extraction device.
Figure 4C:
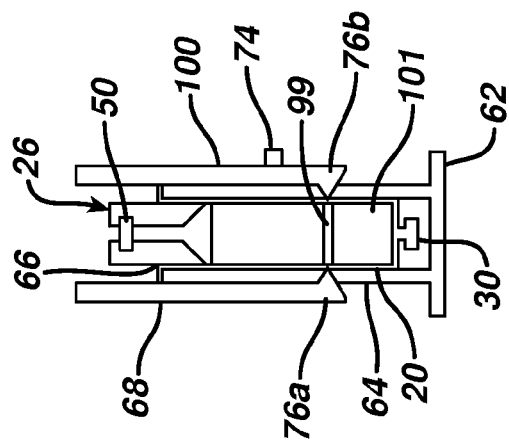
FIG. 4C is a plan view of extracting an excess amount of PPP to the PPP syringe using the extraction device.

In FIG. 4B, an empty PPP syringe 91 with barrel 97, plunger 103 and a needle 93 attached at the tip 31 is inserted into the piston assembly 26 with the needle 93 piercing through the seal 50. In FIG. 4C, the PPP syringe 91 is placed into the inner channel 66 of the extraction device 60. The PPP syringe barrel 97 is depressed, pushing down the piston assembly 26 to descend. As the PPP syringe 91 descends, the needle 93 will enter into the blood container 20, pierce through the seal 50 and will come in contact with the PPP 100 in the blood container 20. The excess PPP 100b will flow into the PPP syringe barrel 97 until the flange 95 comes in contact with the top of the sleeve 68, leaving behind a predetermined amount of PPP 100a. The predetermined volume is small, which is designed to maximize the PRP extraction without unduly disturbing the buffy coat layer in the process of extracting the excess PPP. In one embodiment, a predetermined amount of PPP remaining is about 0.8 cc. The PPP syringe 91 is then removed after collecting the excess PPP 100b. A doctor can then administer the PPP 100b to a patient as an adjunct to healing and hemostasis.

Figure 4D:
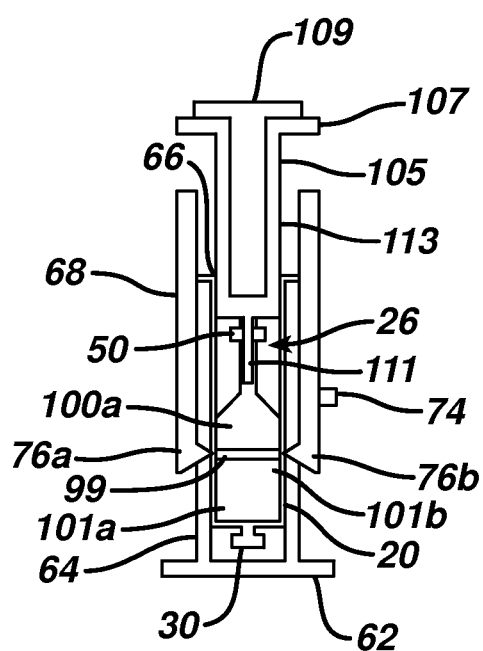
FIG. 4D is a plan view of inserting the PRP syringe into the extraction device after extracting the excess amount of PPP.
Figure 4E:
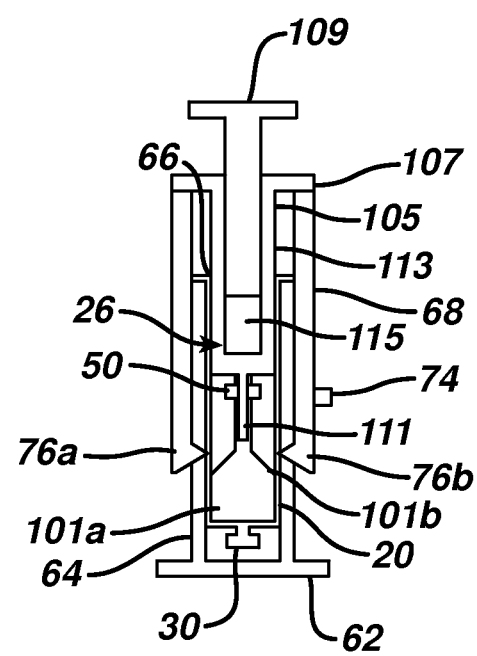
FIG. 4E is a plan view of extracting a predetermined amount of PRP to the PRP syringe using the extraction device.

In FIGS. 4D-4E, a PRP syringe 105 with barrel 113, plunger 109 and needle 111 is inserted into the inner channel 66 through seal 50 to extract a predetermined amount of PRP. The barrel 113 is pressed down until the flange 107 comes in contact with the top of the sleeve 68. As the barrel 113 descends, so does the piston assembly 26. The needle 111 will come in contact with and extract the remaining amount of PPP 101a, and then the buffy coat layer 99, and finally a predetermined amount of red blood cells 101b into barrel 113. In one embodiment, the predetermined volume of red blood cells 101b is about 0.8 cc and the volume of the buffy coat layer 99 is about 01. To 0.2 cc. The mixture of the extracted PPP 101b, the buffy coat layer 99, and red blood cells 101b becomes the PRP 115. A doctor can then administer the PRP 115 to a patient for healing and hemostasis purpose.

FIGS. 4F-4J depict an alternative embodiment of the PPP syringe 91 and the PRP syringe 105.

Figure 4F:
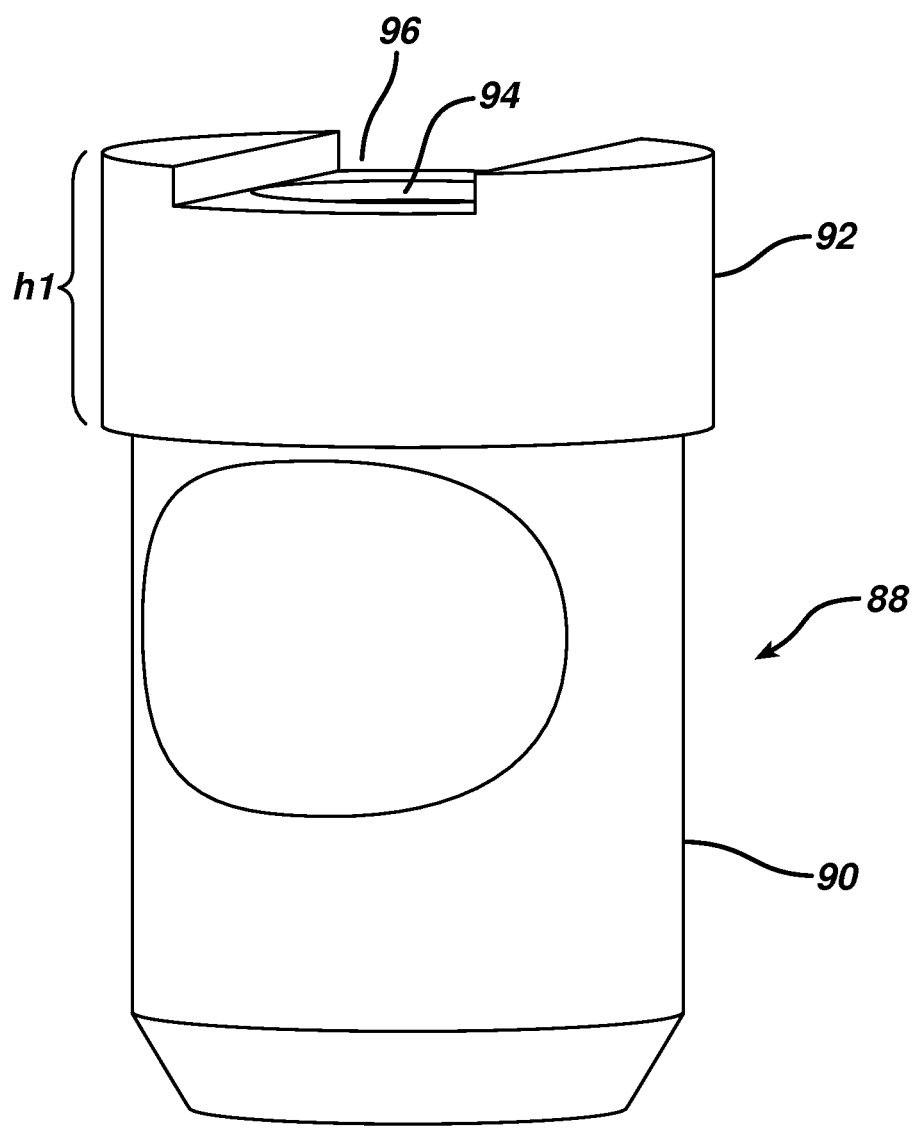
FIG. 4F is a front perspective view of a PPP stopper used in an alternative embodiment of the PPP syringe in FIG. 4B.
Figure 4G:
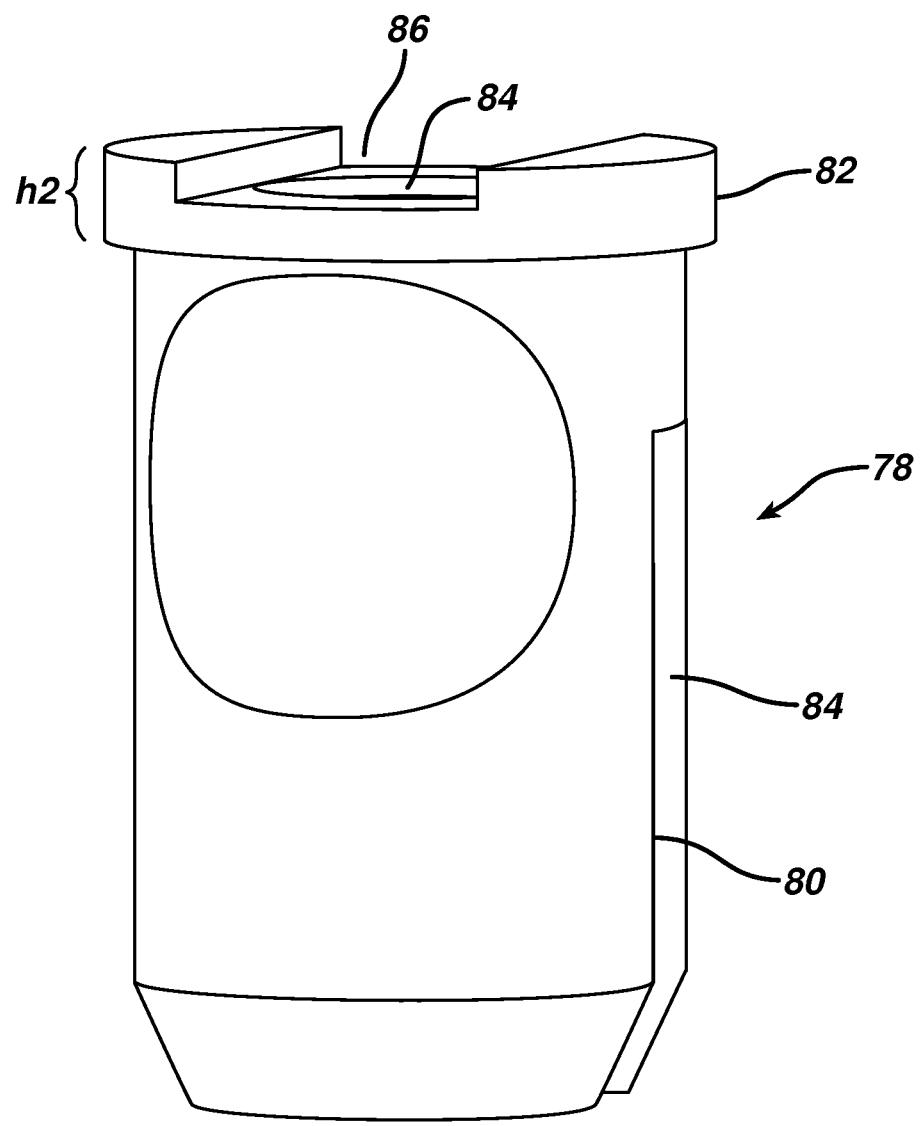
FIG. 4G is a front perspective view of a PRP stopper used in an alternative embodiment of the PRP syringe in FIG. 4D.
Figure 4H:
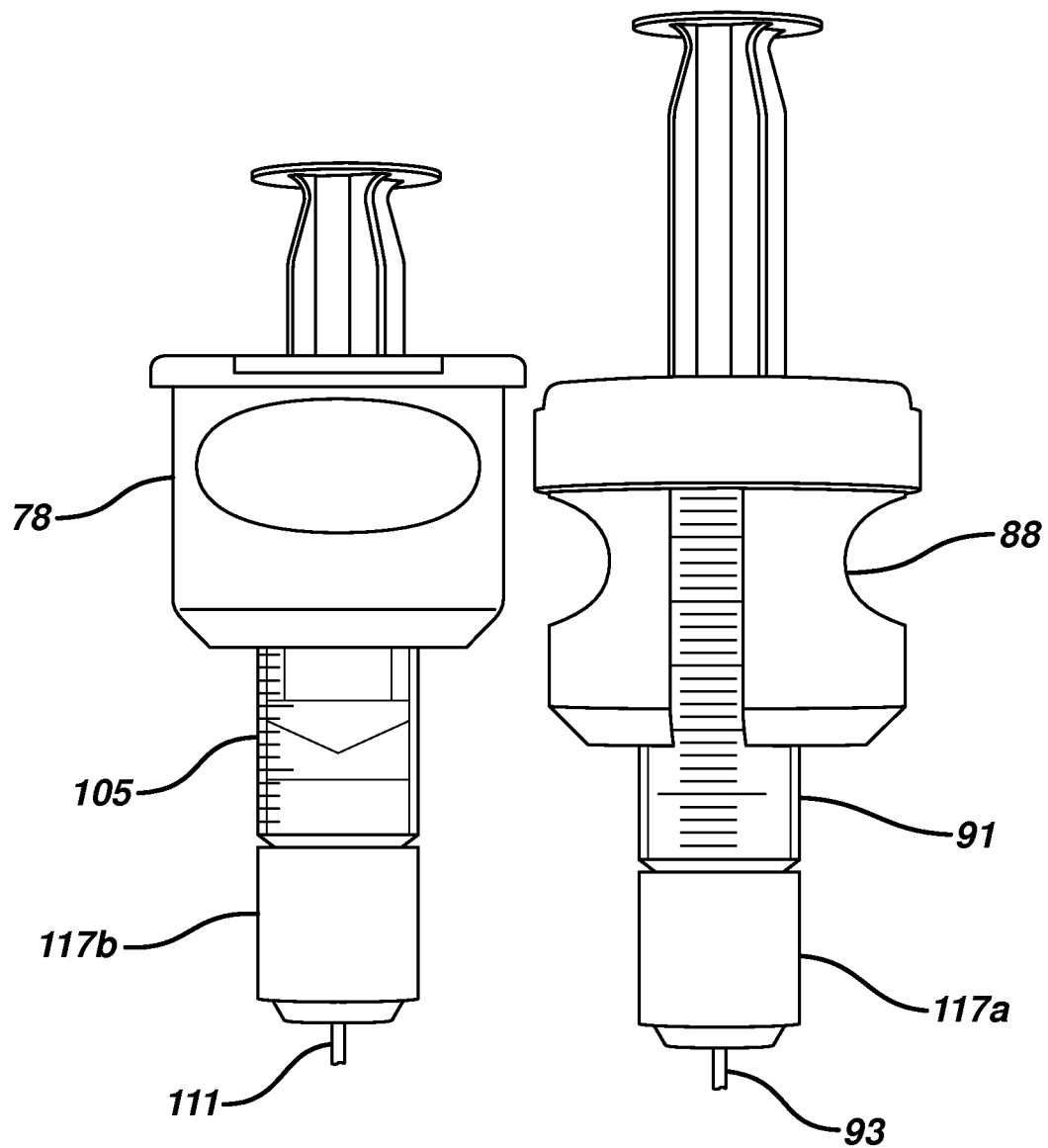
FIG. 4H is a front perspective view of the PPP stopper and the PRP stopper loaded onto the PPP syringe and the PRP syringe with the spacers respectively.

In FIG. 4F, a PPP stopper 88 is added to the PPP syringe 91 (as shown in FIG. 4H). The PPP stopper has a body 90 that has generally the same diameter as the inner portion 70 of the sleeve 68 and an enlarged head 92 formed integrally at the upper end of the body. The enlarged head 92 has a depth of h1. A cylindrical channel 94 is formed at the central portion of the PRP stopper 88 and goes through the enlarged head 92 and the body 90. Both the upper and the lower end of the cylindrical channel 94 are open. A depression 96 is formed above the top of the cylindrical channel 84 to hold the flange 95 of the PPP syringe 91 during the PPP extraction process.

FIG. 4G depicts a PRP stopper 78 which is added to the PRP syringe 105 (as shown in FIG. 4H). The PRP stopper 78 has a body 80 that has generally the same diameter as the inner portion 70 of the sleeve 68 and an enlarged head 82 formed integrally at the upper end of the body. The enlarged head 82 has a depth of h2. A cylindrical channel 84 is formed at the central portion of the PRP stopper and goes through the enlarged head 82 and the body 80. Both the upper and the lower end of the cylindrical channel are open. A depression 86 is formed above the top of the cylindrical channel 84 to hold the flange 107 of the PRP syringe 105 during PRP extraction process.

In FIG. 4H, after inserting the PPP syringe 91 and the PRP syringe 105 into the PPP stopper 78 and the PRP stopper 88 respectively, the PPP needle 93 and the PRP needle 111 are inserted through a PPP spacer 117a and a PRP spacer 117b respectively. The difference between the enlarged head 92 of the PPP stopper 88 and the enlarged head 82 of the PRP stopper 78 correspond to a predetermined volume of PRP to be extracted.

Figure 4I:
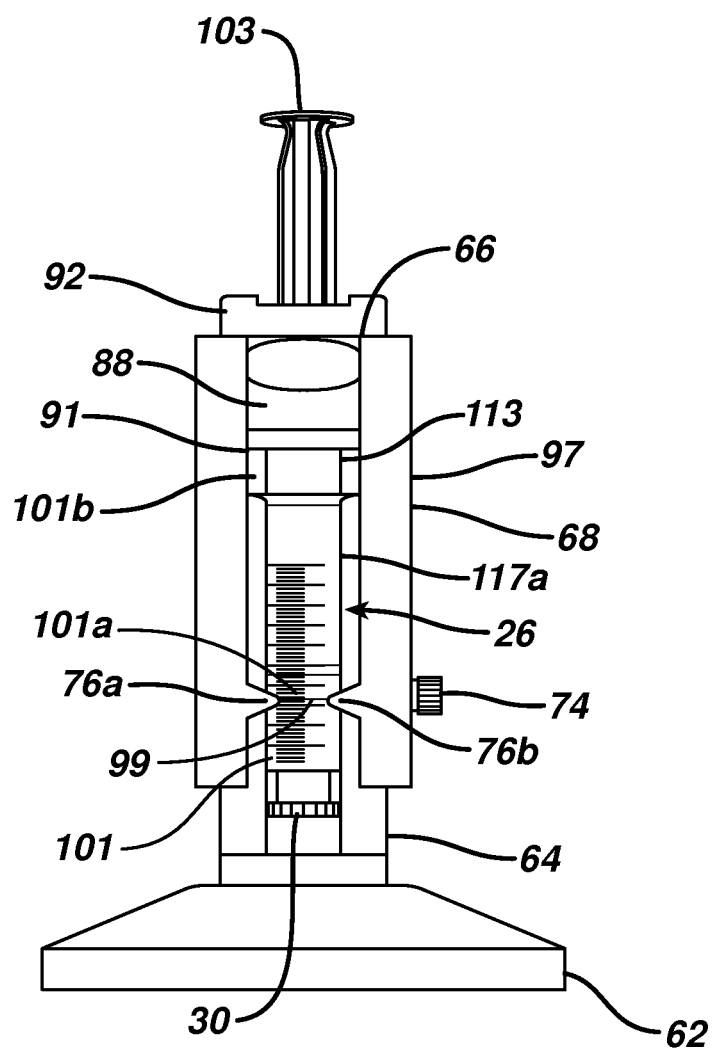
FIG. 4I is a front perspective view of the exaction device extracting an excess amount of PPP with the PPP syringe loaded with the PPP stopper and spacer.

In FIG. 4I, the PPP syringe 91 loaded with the PPP stopper 88, the spacer 117a, the barrel 97, the plunger 103 and the needle 93 (not shown) is inserted into the inner channel 66. The barrel 97 is pressed down along with the PPP stopper 88, causing the needle 93 to pierce through the seal 50 (not shown) and come in contact with the PPP 100 (not shown) in the blood container 20. An excess amount of PPP 100b will flow into the PPP syringe barrel 97 until the bottom of the enlarged head 92 comes in contact with the top of the sleeve 68, leaving behind a predetermined amount of PPP 100a. The PPP syringe 91 is then removed after collecting the excess amount of PPP 100b. A doctor can then administer the PPP 100b to a patient an adjunct to healing and hemostasis.

Figure 4J:
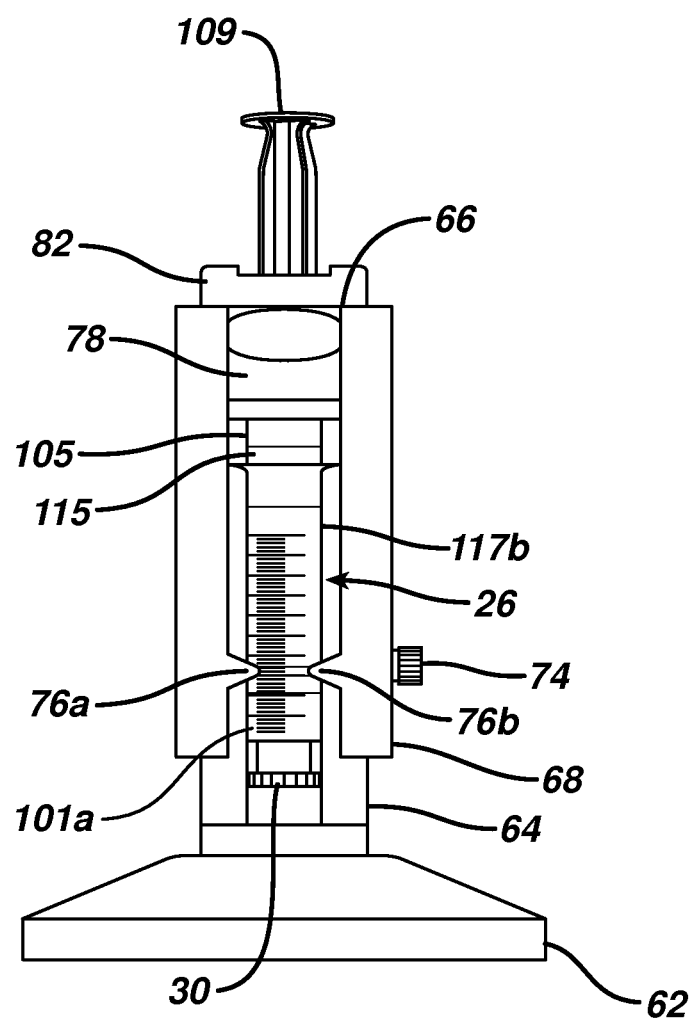
FIG. 4J is a front perspective view of the exaction device extracting a predetermined amount of PRP with the PRP syringe loaded with the PRP stopper and spacer.

In FIG. 4J, the PRP syringe 105 loaded with the PRP stopper 78, the spacer 117b, the barrel 113, the plunger 109 and the needle 111 (not shown) is inserted into the inner channel 66 through seal 50 to extract a predetermined amount of PRP. The barrel 113 is pressed down along with the PRP stopper 78 until the bottom of the enlarged head 82 comes in contact with the top of the sleeve 68. As the barrel 113 descends, the piston assembly 26 descends as well. The needle 111 will come in contact with and extract the remaining amount of PPP 100a (not shown), and then the buffy coat layer 99 (not shown), and finally a predetermined amount of red blood cells 101b (not shown) into barrel 113. The mixture of the extracted PPP 101b, the buffy coat layer 99, and red blood cells 101b becomes the PRP 115. A doctor can then administer the PRP 115 to a patient for healing and hemostasis purpose.

Figure 5:
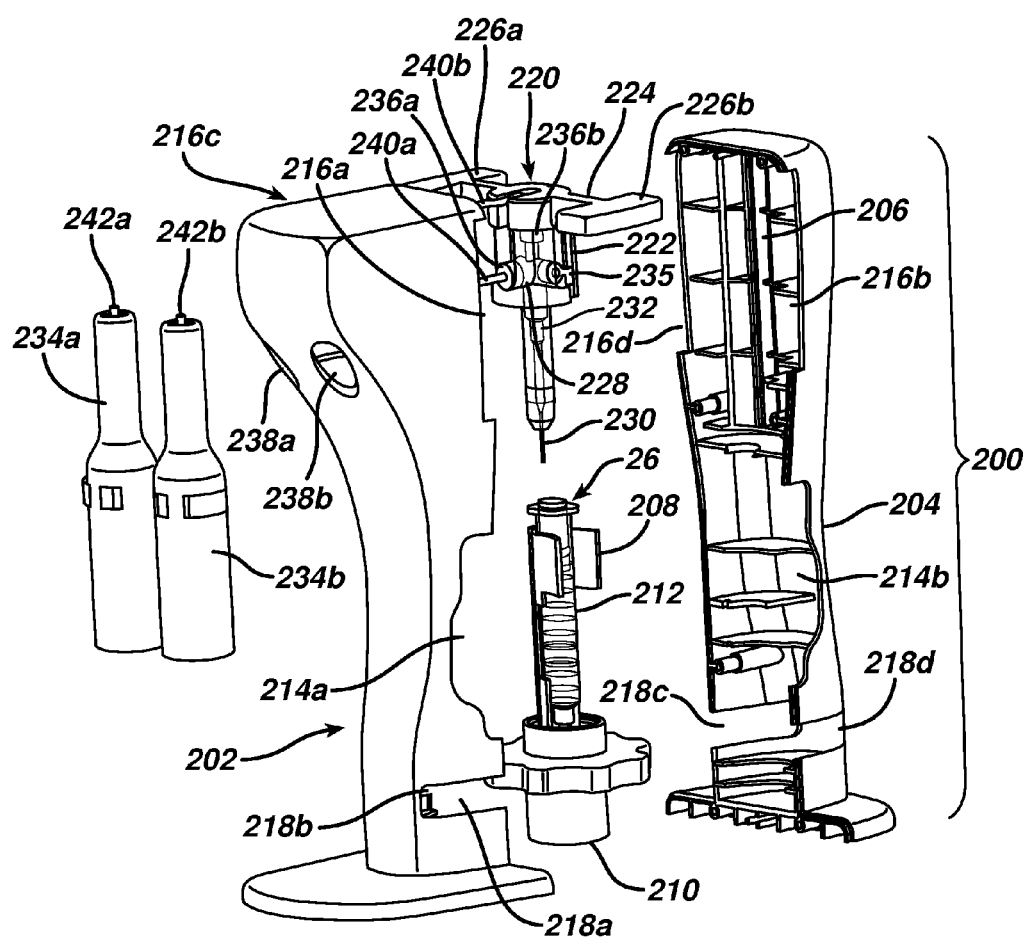
FIG. 5 is an exploded view of an alternative embodiment of the extraction device.

Turning now to FIG. 5 which illustrates an alternative embodiment of the invention. An extraction device 200 has a front housing member 202, a back housing member 204, which is connected to the front housing member 202 in the assembled extraction device 200. An internal rib structure 206 in the back housing member 204 and the internal rib structure in the front housing member (not shown) hold the internal components of the assembled extraction device 200 in place and provide rigidity. A holder 208 is threadably connected to an adjustment knob 210 disposed within the extraction device 200. A blood container 212 is placed into the blood container holder via open space created by side channels 214a, 214b of the front housing member 202 and the back housing member 204 respectively. The adjustment knob 210 is exposed via open space created by lower side channels 218a, 218b of the front housing member 202 and lower side channels 218c, 218d of the back housing member 204 respectively. This allows the holder 208 to be raised or lowered by turning the adjustment knob 210, which in turn raises or lowers the blood container 212. An extraction assembly 220 is disposed within the extraction device 200 above the blood container 212. The extraction assembly 220 has a housing member 222 and a handle 224 with handle bars 226a, 226b. The handle bars 226a, 226b are exposed via open space formed by side channels 216a, 216c of the front housing member 202 and side channels 216b, 216d of the back housing member 204. Disposed within the housing member 222 is a stopcock valve 228 and an extraction needle 230 attached to a valve inlet 232 of the stopcock valve 228. A handle 235 connects to the stopcock valve 228 to control the fluid flow and is exposed outside of the housing member 222. A PPP extraction container 234a (not shown) disposed within an optional PPP cover 242a is connected to a valve outlet 236a of the stopcock valve 228 via an aperture 238a of the front housing member 202 and via a tube 240a. A PRP extraction container 234b (not shown) disposed within an optional PRP cover 242b is also connected to a valve outlet 236b of the stopcock valve 228 in the same way via an aperture 238b and a tube 240b. The PPP and PRP extraction containers can be syringe barrels with plungers attached. In one embodiment, the PPP and PRP extraction containers are the BD 5 cc syringes.

Figure 6:
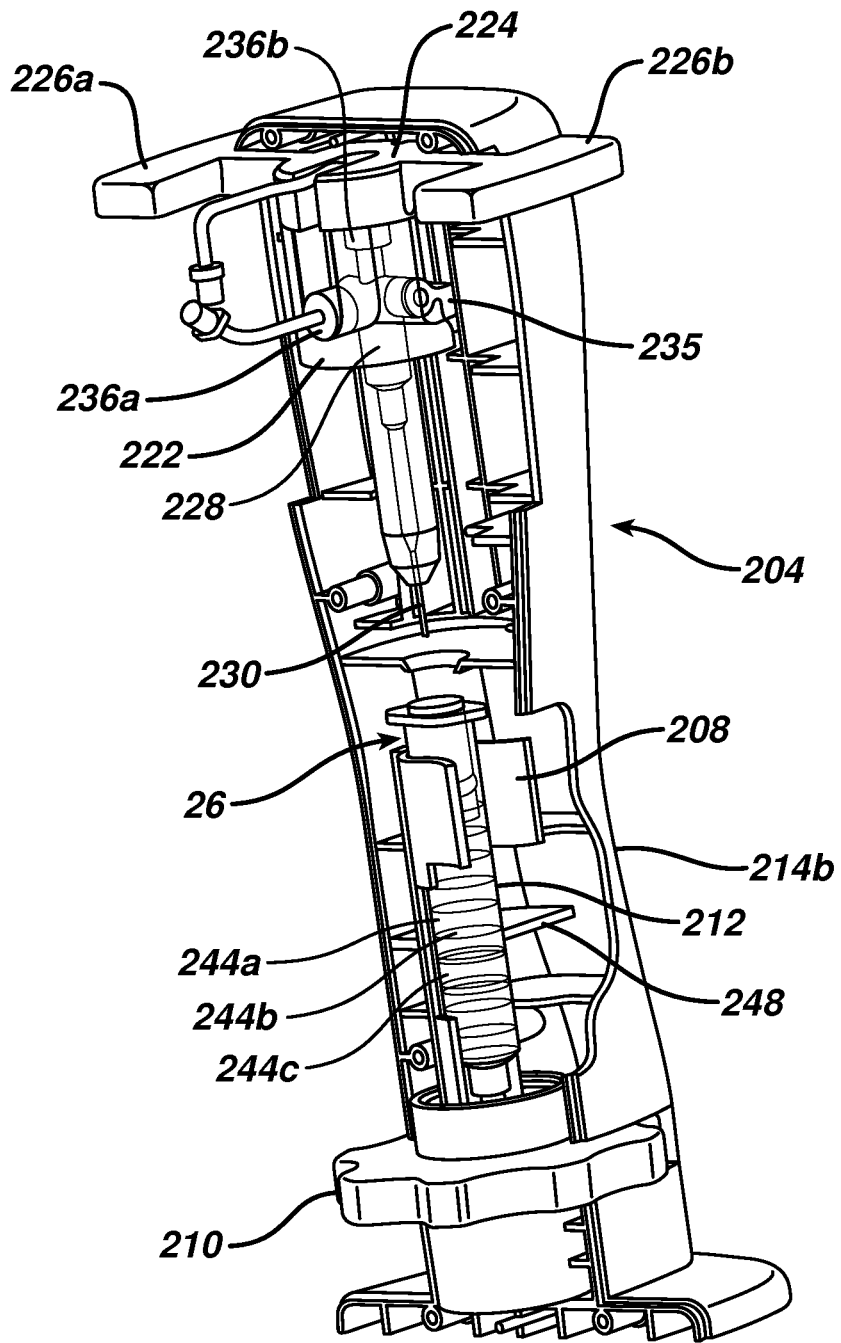
FIG. 6 is a front perspective view of aligning the buffy coat layer with the indicator rib of the extraction device in FIG. 5.

FIG. 6 describes the operation of the extraction device 200 in FIG. 5 to extract PPP and a predetermined amount of PRP. After a whole blood sample is collected into the blood container 212 and is centrifuged, the blood container 212 with the post centrifuged whole blood sample in placed into the holder via the side channels 214a (not shown in FIG. 6)

and 214b. Inside the blood container 212, the whole blood sample has three layers, a PPP layer 244a on top, a buffy coat layer 244b under the PPP player 244a, and a red blood cells layer 244c at the bottom. The adjustment knob 210 is turned to either raise or lower the blood container so that the buffy coat layer 244b is aligned with an indicator rib 248.

Figure 7:
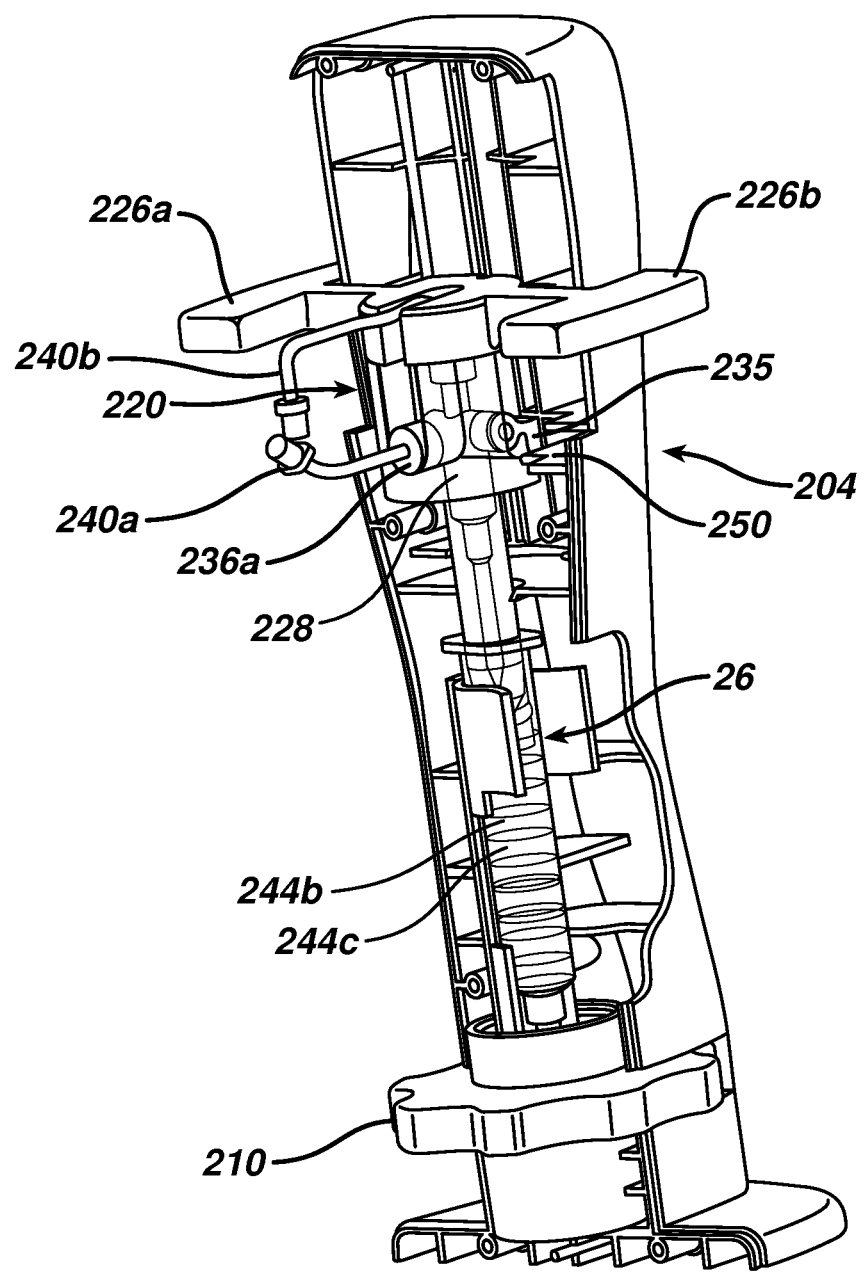
FIG. 7 is a front perspective view of the extraction device extracting an excess amount of PPP.
Figure 8:
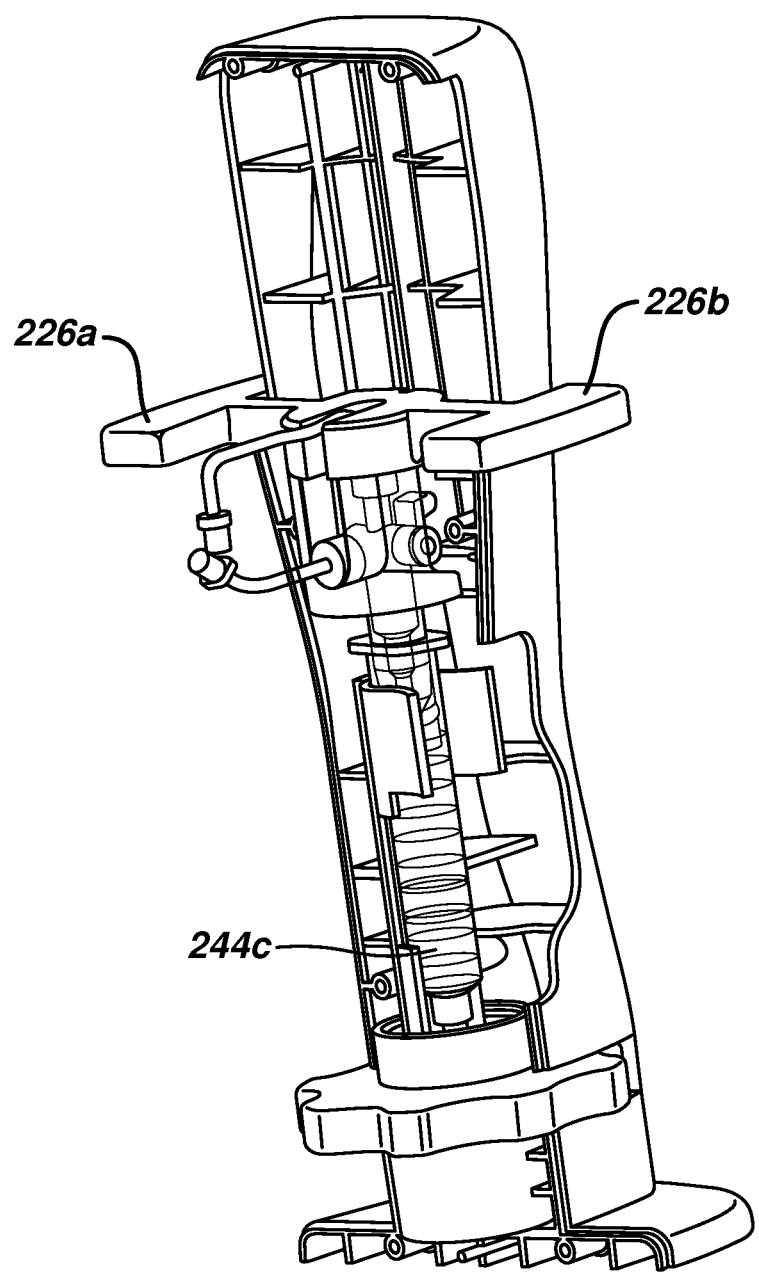
FIG. 8 is a front perspective view of the extraction device extracting a predetermined amount of PRP.

Turning to FIG. 7, after the buffy coat layer 244b has been aligned with the indicator rib 248, the handle bars 226a and 226b are pressed down to start the extraction process. As the handle bars descend, they push the extraction assembly 220 downward. The needle 230 (not shown) will come in contact with the piston 34 and pierce through the seal 50 (not shown), then the needle 230 will come in contact with the PPP layer 244b. The stopcock handle 235 is at an initial position, which allows an excess amount of PPP to be extracted through the needle 230, the valve inlet 232, the valve outlet 236a, tube 240a of the stopcock valve 228, and into the PPP extraction container 234a (not shown). After the extraction assembly 220 has descended for a certain distance, the handle 235 of the stopcock valve 228 comes in contact with an activation rib 250 and the handle 235 is gradually turned upward. As the handle 235 is turning upward, the fluid flow inside the stopcock valve 228 changes so that some amount of PPP will continue to flow into the PPP extraction container 234a and some amount of PPP will start flowing into the PRP extraction container 234b (not shown). Once the handle 235 is turned ninety degree upward into a final position, the fluid flow change inside the stopcock valve 228 is complete and there will be only fluid flowing into the PRP extraction container 234b. After the handle 235 is turned to the final position and as the handle bars 226a and 226b continue to descend until they come in contact with the bottom edges of the side channels 216a-216d. A predetermined amount of the PPP, the buffy coat layer 244b and a predetermined amount of red blood cells are collected into the PRP extraction container 234b. Only a remaining amount red blood cells 245 are left in the blood container (as shown in FIG. 8). Thus, an excess amount of PPP and a predetermined amount of PRP are extracted continuously and in a sequence by pushing the handle bars 226a and 226b all the way down in a single motion. A doctor can then administer the PPP an adjunct to healing and hemostasis and the PRP to a patient for healing and hemostasis purpose.

Figure 9:
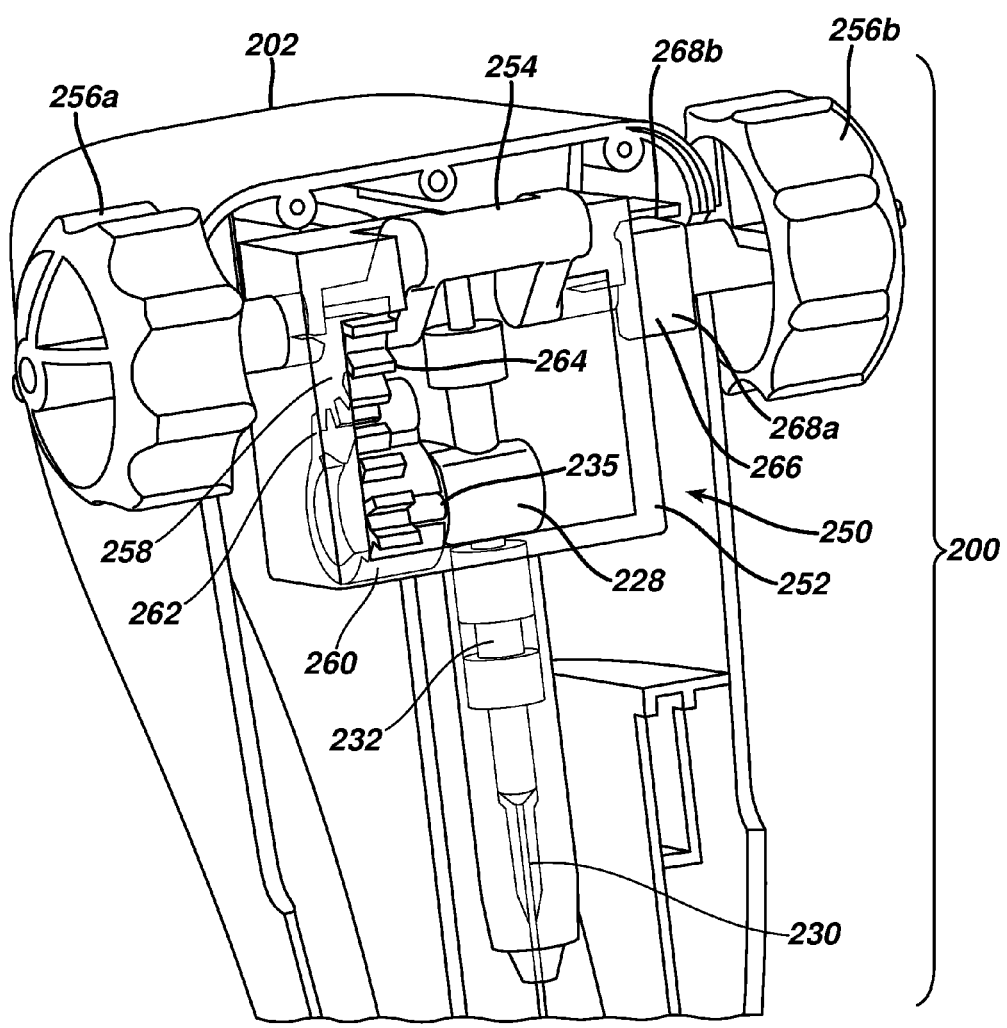
FIG. 9 is a back perspective view of an alternative embodiment of the extraction assembly.
Figure 10:
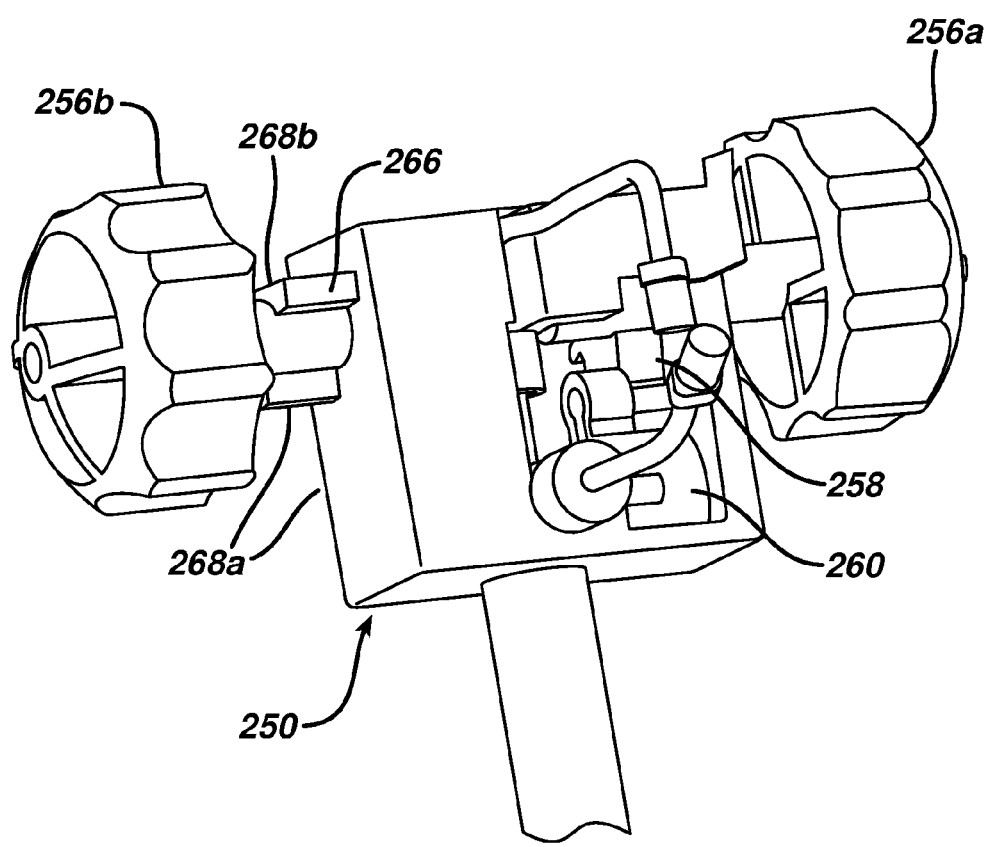
FIG. 10 is a front perspective view of the extraction assembly in FIG. 9.

FIG. 9 depicts an alternative embodiment of an extraction assembly in the extraction device 200 in FIG. 5. The extraction assembly 250 has a housing 252 with handle 254 disposed within. The handle 254 has turning knobs 256a and 256b at each end respectively, which are located outside of the housing 252 and the extraction device 200. A first turning gear 258 is integrally molded into the handle 254. Also disposed within the housing 252 is the stopcock valve 228 with the needle 230 attached to the inlet port 232 of the stopcock valve 228. The handle 235 of the stopcock valve 228 is fitted into a second turning gear 260, which is connected to the first turning gear 258 via gear teeth 262 and 264. A stopper 266 is also integrally molded into the handle 254 with a front side 268a and an up side 268b (as shown in FIG. 10).

Figure 11:
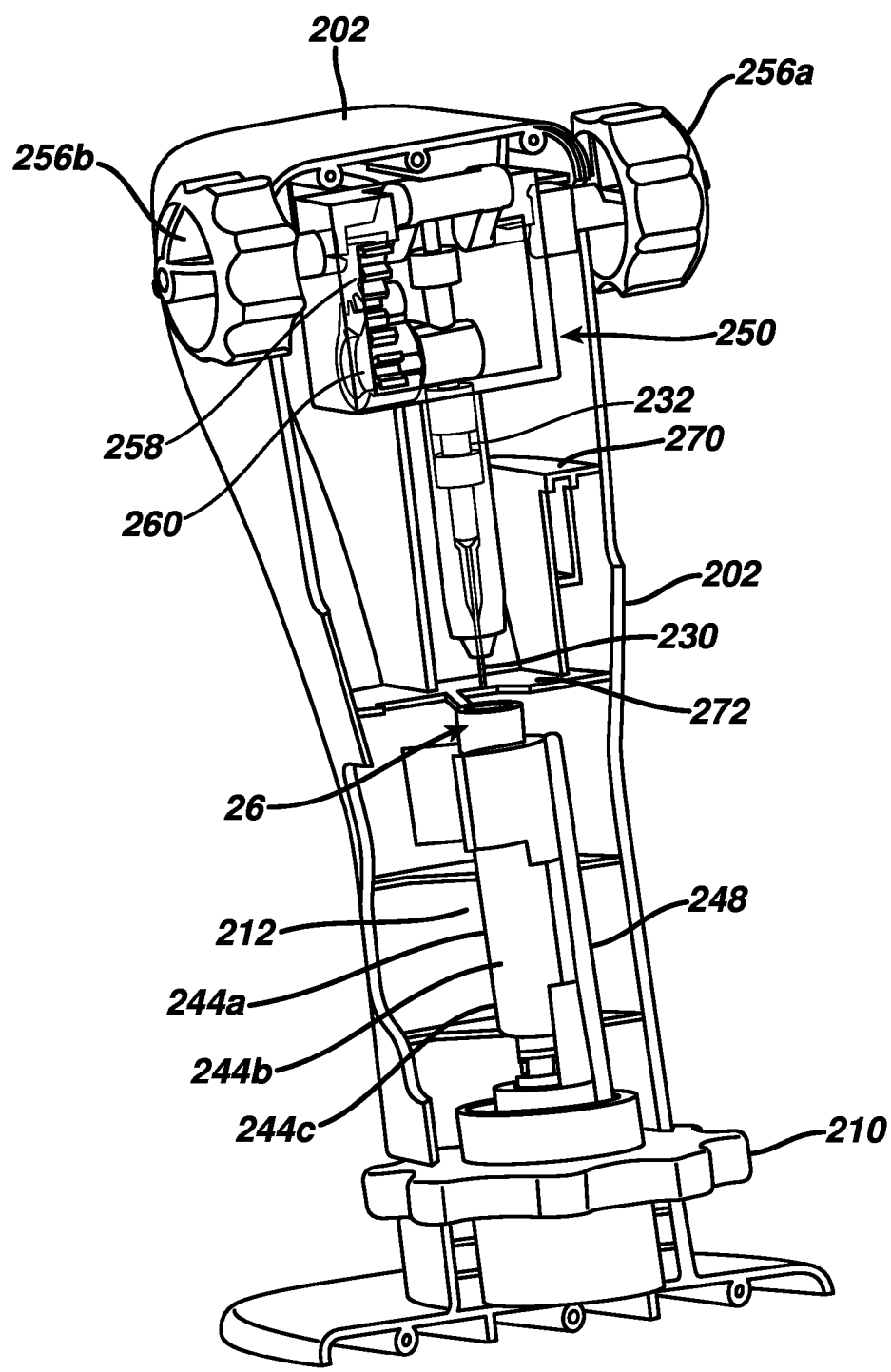
FIG. 11 is a back perspective view of the extraction device with the extraction assembly in FIG. 9.
Figure 12:
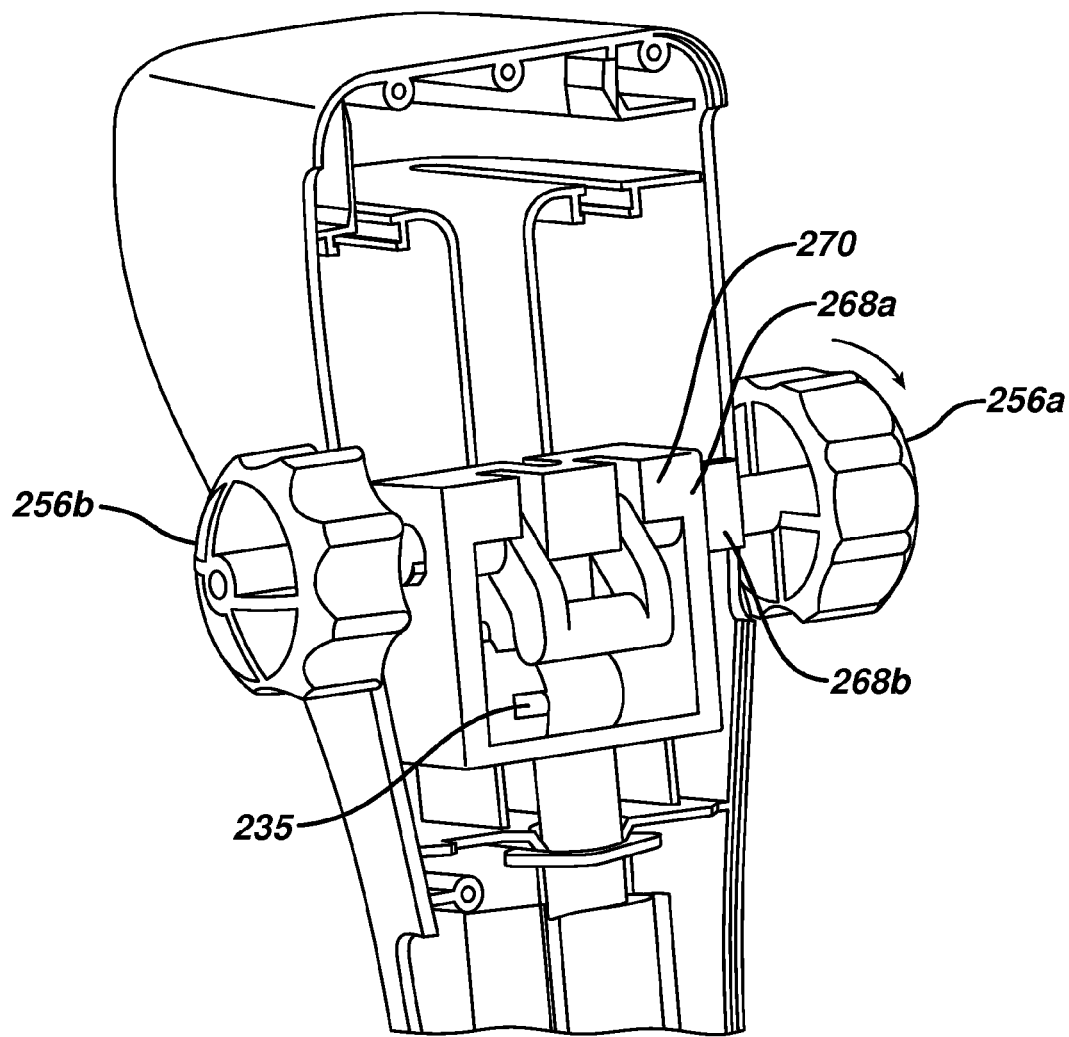
FIG. 12 is a front perspective view of the switch from extracting PPP to PRP in the extraction assembly.
Figure 13:
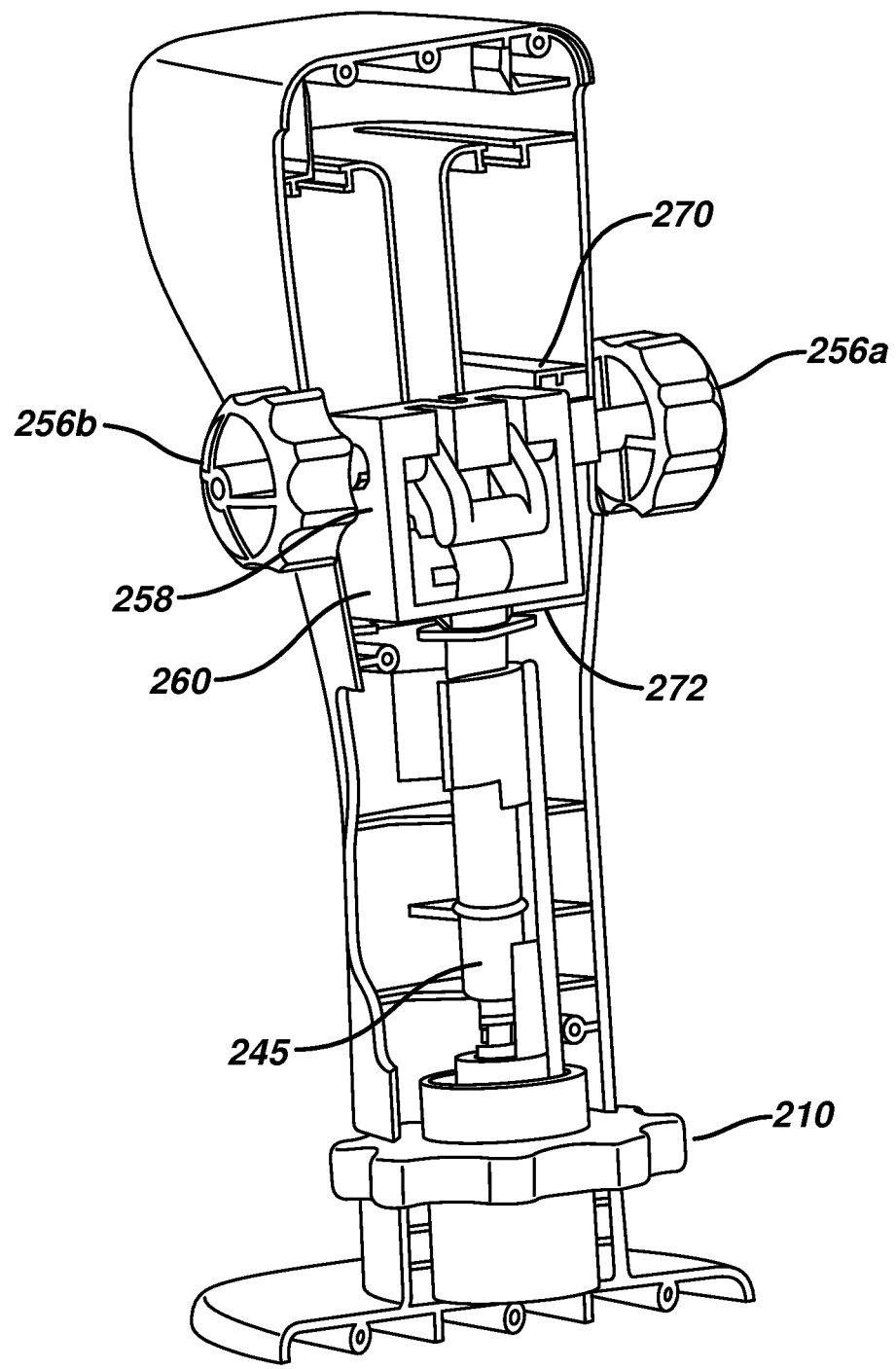
FIG. 13 is a front perspective view of the extraction assembly after the predetermined amount of PRP has been extracted.

FIGS. 11-13 depict the PPP and PRP extraction process with the extraction assembly 250 in FIG. 9. In FIG. 11, after the buffy coat layer 244b has been aligned with the indicator rib 248, the handle 254 is pressed down by pressing down on the turning knobs 256a and 2256b to start the extraction process by a user. As the handle 254 is coming down, it is pushing the extraction assembly 250 down as well. The needle 230 will come in contact with the piston assembly 26 and pierce through the seal 50 of the piston assembly 26, and then the needle 230 will come in contact with the PPP 244a. The stopcock valve 228 is at an initial position, which allows the PPP 244a to be extracted through the needle 230, the valve inlet 232, the valve outlet 236a (as shown in FIG. 7), the tube 240a (as shown in FIG. 7), into the PPP extraction container 234a (not shown). The PPP will be extracted until the up side of the stopper comes in contact with a blocking rib 270 (as shown in FIG. 12), located in the front housing member 202. The blocking rib prevents the extraction assembly 250 from moving further down and acts a signal to a user that an appropriate amount of PPP has been extracted.

In FIG. 12, the knobs 256a, 256b on the handle 254 are turned ninety degrees backward as indicated by the direction of the arrow by the user. The turning of the handle bar will cause the front 268a and up side 268b to rotate ninety degrees backward as well. The up side 268b will be in front of the blocking rib 270, while the front side 268a will be below the blocking rib 270, thus the blocking rib 270 will no longer prevent the extraction assembly 250 from moving down. Also, as the handle bars 256a, 256b are rotated, the first turning gear 258 caused the second turning gear 260, changing the fluid flow in the stopcock from PPP to PRP.

In FIG. 13, the user again pressed the knobs 256a, 256b down to collect PRP, the predetermined amount of PRP will be collected until the bottom of the housing comes in contact with a second blocking rib 272 (as shown in FIG. 11), leaving behind only a remaining amount of red blood cells 245.

Figure 14:
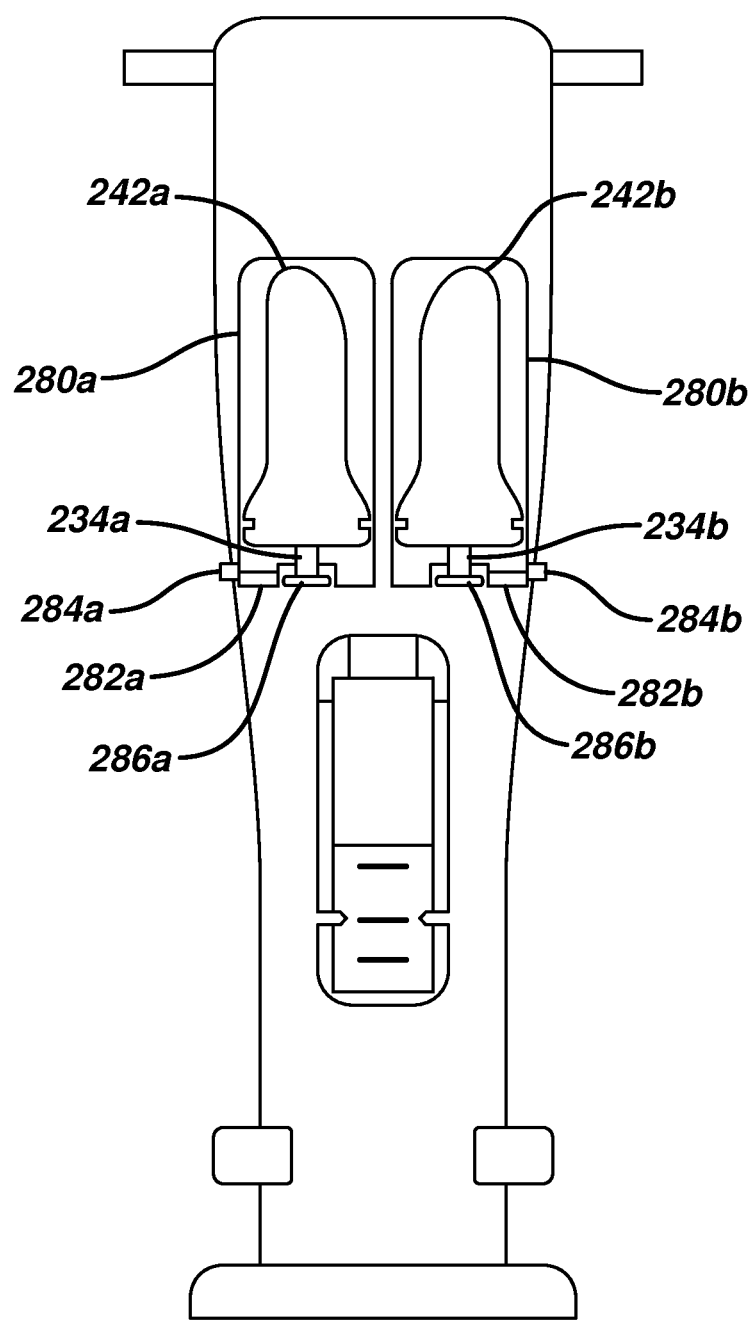
FIG. 14 is a front perspective view of an alternative embodiment of the PPP cover and PRP cover.

FIG. 14 shows an alternative embodiment with the optional PPP cover 242a and PRP cover 242b. Protective sleeves 280a and 280b in a compressed form slip over the PPP cover 242a and the PRP cover 242b respectively, which in turn cover the PPP extraction container 234a and the PRP extraction container 234b respectively. In one embodiment, the PPP extraction container 234a and the PRP extraction container 234b are BD 10 cc syringes. The protective sleeves 280a and 280b threadably attach to the front housing member 202. At the bottom of the protective sleeves 280a and 280b, a grasping member 282a and 282b will clip onto the plunger 286a, 286b of the PPP extraction container 234a and the PRP extraction container 234b respectively. Release button 248a and 248b are connected to the grasping members 282a and 282b respectively to release the PPP extraction containers 234a and the PRP extraction container 234b respectively.

Figure 15:
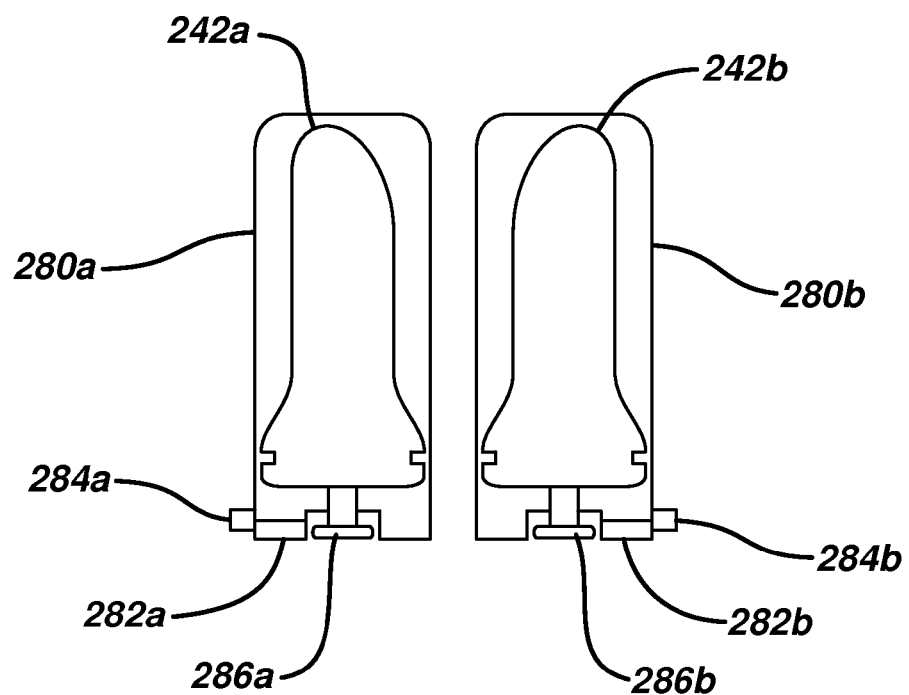
FIG. 15 is a front perspective view of the PPP cover and PRP cover in operation.

Turning to FIG. 15, as either the PRP extraction container 234a or the PRP extraction container 234b is filled, the plunger 286a or 286b will be pushed downward, stretching the protective sleeve 280a or 280b to keep the extraction container 234a or 234b sterile. After the extraction is done, the PPP container 234a or the PRP container 234b is disconnected to the tube 240a or 240b, and then the release button 248a or 248b is pressed to disconnect the appropriate grasping member from the appropriate container. The appropriate container will then drop into any desired containers for transportation without being handled manually. The protective sleeves 280a and 280b can be of plastic or any other suitable material well known in the art.

Various modifications and alterations of this invention will be apparent to those skilled in the art without departing from the scope and spirit of this invention. It should be understood that the invention is not limited to the embodiments disclosed herein, and that the claims should be interpreted as broadly as the prior art allows.

What is claimed is:

1. A method for procuring platelet rich plasma (PRP) from a sample of whole blood in a vial, the method comprising the steps of:
    separating the whole blood into layers through centrifugation with an upper layer containing platelet poor plasma (PPP) and a PRP layer disposed below the upper layer and containing PRP;
    adjusting an end point of a first range of motion of an extractor relative to a position of the PRP layer by setting the position of a stop against which an abutment associated with the extractor engages at the end point, the position of the stop being determined by aligning with the PRP layer an indicator associated with the stop;
    moving the extractor through the first range of motion through the vial, PPP passing out from the upper layer through the extractor; and
    after the extractor reaches the end point of the first range of motion, extracting the PRP through the extractor and collecting the PRP.

2. The method of claim 1 wherein the sample of whole blood is collected from a patient and further comprising the step of applying the PRP to a site on the patient's body to promote healing.

3. The method of claim 1 wherein the extractor comprises a piston sized to tightly fit through the vial and wherein the PPP passes out of the upper layer through an orifice in the piston.

4. The method of claim 3 wherein the step of extracting the PRP comprises passing a tip of a needle through the orifice to the PRP layer and extracting the PRP through the needle.

5. The method of claim 3 wherein the step of extracting the PRP comprises moving the piston beyond the end point of the first range of motion through a second range of motion and passing the PRP through the orifice while moving the extractor through the second range of motion.

6. The method of claim 5 wherein the orifice is disposed at a distal tip of a needle in the extractor.

7. The method of claim 5 wherein a handle is associated with the extractor and a user in one continuous motion, by pressing on the handle, moves the extractor through the first range of motion and the second range of motion.

8. The method of claim 5 and further comprising the step of passing the PPP through a first flow path as the extractor moves through the first range of motion and engaging a diverter as the extractor reaches the end point, the diverter sending the PRP through a separate second flow path.

9. The method of claim 8 wherein an abutment associated with the extractor engages a lever on the diverter as the extractor reaches the end point to send flow from the extractor through the second flow path.

10. The method of claim 9 wherein the diverter comprises a three-way valve.

* * * * *